United States Patent [19]

Zamboni et al.

[11] Patent Number: 5,232,916
[45] Date of Patent: Aug. 3, 1993

[54] QUINOLINE ETHER ALKANOIC ACIDS

[75] Inventors: Robert Zamboni, Point-Claire; Petpiboon Prasit, Kirkland; Robert N. Young, Senneville, all of Canada

[73] Assignee: Merck Frosst Canada, Inc., Kirkland, Canada

[21] Appl. No.: 783,463

[22] Filed: Oct. 28, 1991

Related U.S. Application Data

[63] Continuation of Ser. No. 453,654, Dec. 20, 1989, Pat. No. 5,102,881, which is a continuation-in-part of Ser. No. 211,642, Jun. 27, 1988, abandoned.

[51] Int. Cl.$^5$ .................. C07D 215/14; A61K 31/47
[52] U.S. Cl. ................... 514/151; 514/228.2; 514/233.5; 514/255; 514/311; 514/312; 514/313
[58] Field of Search .......... 544/62, 128, 363; 546/153, 159, 172, 174, 175; 514/312, 311, 313, 255, 233.5, 228.2, 151

[56] References Cited

U.S. PATENT DOCUMENTS

| | | | |
|---|---|---|---|
| 4,631,287 | 12/1986 | Chakraborty et al. | 546/153 |
| 4,661,499 | 4/1927 | Young et al. | 514/312 |
| 4,683,325 | 7/1987 | Frenette et al. | 549/299 |
| 4,769,461 | 9/1988 | Musser et al. | 946/153 |
| 4,794,188 | 12/1988 | Musser et al. | 546/176 |
| 4,803,211 | 2/1989 | Mose et al. | 514/361 |
| 4,839,369 | 6/1989 | Yoursefyeh et al. | 546/152 |
| 4,851,409 | 7/1989 | Young et al. | 546/154 |
| 4,920,130 | 4/1990 | Huang et al. | 546/153 |
| 4,920,131 | 4/1990 | Huang et al. | 514/312 |
| 4,920,133 | 4/1990 | Huang et al. | 546/153 |

FOREIGN PATENT DOCUMENTS

| | | | |
|---|---|---|---|
| 0219307 | 4/1987 | European Pat. Off. | 514/314 |
| WO87/05510 | 9/1987 | European Pat. Off. | 514/311 |
| 271287 | 6/1988 | European Pat. Off. | 546/175 |
| 0339416 | 2/1989 | European Pat. Off. | 546/153 |
| 0344519 | 5/1989 | European Pat. Off. | 514/311 |
| 0348155 | 12/1989 | European Pat. Off. | 514/312 |

OTHER PUBLICATIONS

Sakamoto, Chem. Pharm. Bull. 32(6) 2241-2248 1984.
J. Med. Chem. vol. 21, (8) 1978, Saari et al. pp. 746-753.
Bundgaard et al. J. Med. Chem. 30(3) 1987 pp. 451-453.
Hackh's Chemical Dictionary, 4th Ed. p. 27 (1969).

*Primary Examiner*—Mukund J. Shah
*Assistant Examiner*—E. C. Ward
*Attorney, Agent, or Firm*—Gabriel Lopez; Joseph F. DiPrima

[57] ABSTRACT

Compounds having the formula:

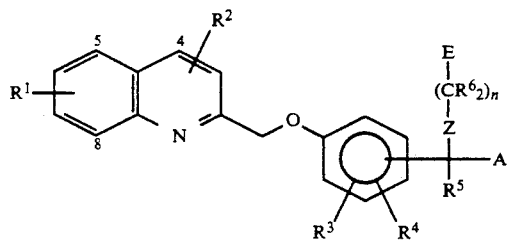

are inhibitors of leukotriene biosynthesis. These compounds are useful as anti-asthmatic, anti-allergic, anti-inflammatory, and cytoprotective agents. They are also useful in treating diarrhea, hypertension, angina, platelet aggregation, cerebral spasm, premature labor, spontaneous abortion, dysmenorrhea, and migraine.

2 Claims, No Drawings

QUINOLINE ETHER ALKANOIC ACIDS

CROSS-REFERENCE

This is a continuation of application Ser. No. 453,654, filed Dec. 20, 1989, now U.S. Pat. No. 5,102,881, which is a continuation-in-part of U.S. Ser. No. 211,642, filed Jun. 27, 1988, now abandoned.

BACKGROUND OF THE INVENTION

The leukotrienes and their biological activities, especially their roles in various disease states and conditions have been described. For example, see U.S. Pat. No. 4,683,325 (Jul. 28, 1987), which is incorporated herein by reference.

Several classes of compounds exhibit the ability to inhibit the biosynthesis of leukotrienes in mammals, especially humans.

EP 181,568 describes a series of compounds of the general formula:

$Ar_1-X-Ar-Z-(R)n'$ which differ from the present invention in not having a cycloakyl or phenyl substituent (R) attached directly to the alkylene chain Z and does not have the E substituent in the preferred embodiment of the present invention attached by a sulfur atom to the alkylene chain.

U.S. Pat. No. 4,631,287 contains compounds of the formula:

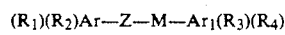

$(R_1)(R_2)Ar-Z-M-Ar_1(R_3)(R_4)$ which differ from the present invention in that the $R_3$ and $R_4$ substituents which contain a carboxy group (corresponding to the E substituent of the present invention) are attached directly to $Ar_1$ by an oxygen atom. Further, when they contain an aryl group, it is either attached directly to $Ar_1$ or is attached through an oxygen atom. Furthermore, $R_3$ or $R_4$ do not simultaneously include the E substituent of the present invention and the cycloalkyl or phenyl substituent of the present invention.

EP 200,101 and Australian Patent application 56398/86 disclose compounds of the formula:

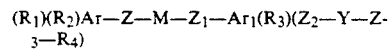

$(R_1)(R_2)Ar-Z-M-Z_1-Ar_1(R_3)(Z_2-Y-Z_3-R_4)$ which differ from the compounds of the present invention in that the substituent unit $(Z_2-Y-Z_3-R_4)$ does not simultaneously contain the cycloalkyl or phenyl and E substituents of the present invention.

W087/05510 discloses compounds of the general formula:

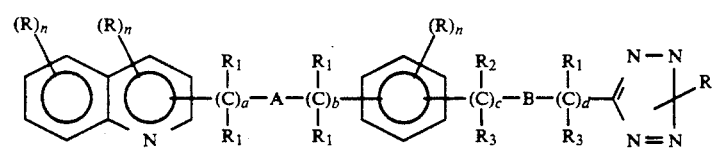

which differ from the compounds of the present invention in that they contain the heterocyclic tetrazole moiety which is absent from the present novel compounds, and in that the phenyl group present in the $R_2$ and $R_3$ substituents is unsubstituted.

SUMMARY OF THE INVENTION

The present invention relates to compounds having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to inhibit the pathologic actions of leukotrienes on the cardiovascular and vascular systems for example, actions such as result in angina or endotoxin shock. The compounds of the present invention are useful in the treatment of inflammatory and allergic diseases of the eye, including allergic conjunctivitis. The compounds are also useful as cytoprotective agents and for the treatment of migraine headache.

Thus, the compounds of the present invention may also be used to treat or prevent mammalian (especially, human) disease states such as erosive gastritis; erosive esophagitis; inflammatory bowel disease; ethanol-induced hemorrhagic erosions; hapatic ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The compounds of this invention are inhibitors of the biosynthesis of 5-lipoxygenase metabolites of arachidonic acid, such as 5-HPETE, 5-HETE and the leukotrienes. Leukotrienes $B_4$, $C_4$, $D_4$ and $E_4$ are known to contribute to various disease conditions such as asthma, psoriasis, pain, ulcers and systemic anaphylaxis. Thus inhibition of the synthesis of such compounds will alleviate these and other leukotriene-related disease states.

DETAILED DESCRIPTION OF THE INVENTION

The compounds of this invention are best realized by Formula I:

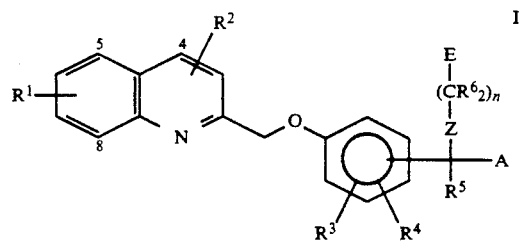

wherein:

A is $-(CR^6{}_2)_m-R^7$ or $-(CR^6{}_2)_p-Z'-(CR^6{}_2)_q-R^{17}$;

Z is $CH_2$, O, or S;

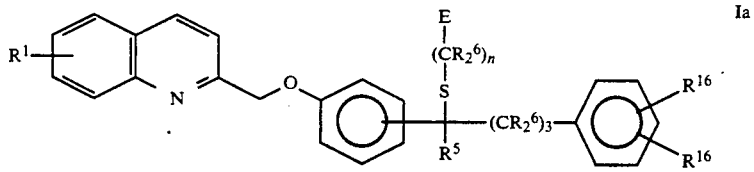

Z' is O or S;
m is 2–4;
n is 1–5;
p is 0–4;
q is 0–4;
s is 0–3;
E is $CO_2R^8$, $CO_2R^{12}$, $-CONHSO_2R^9$, $-CONR^{10}R^{10}$, or $-NHSO_2R^9$;
HET is 2-, 3-, or 4-pyridyl or 2- or 3-thienyl, each of which has two $R^{16}$ substituents;
$R^1$, $R^2$, $R^3$ and R4 are independently H, halogen, $C_1$–$C_6$ alkyl, $C_2$–$C_6$ alkenyl, $C_2$–$C_6$ alkynyl, $-CF_3$, $-OR^{10}$, $-SR^9$, $-S(O)R^9$, $S(O)_2R^9$, $NR^{10}R^{10}$, $-CHO$, $-CO_2R^8$, $-(C=O)R^{11}$, $-C(OH)R^6R^6$, $-CN$, $NO_2$, $N_3$, substituted or unsubstituted phenyl, or substituted or unsubstituted $C_1$–$C_6$ phenylalkyl;
$R^5$ is H, lower alkyl, or phenyl lower alkyl;
each $R^6$ is independently H or lower alkyl, or two $R^6$'s may be joined to form a ring of 3–6 atoms;
$R^7$ is cycloalkyl, or substituted or unsubstituted phenyl;
$R^8$ is H, $C_1$–$C_6$ alkyl, substituted or unsubstituted phenyl, or substituted or unsubstituted benzyl;
$R^9$ is $CF_3$, $C_1$–$C_6$ alkyl, substituted or unsubstituted phenyl, or $C_1$–$C_6$ phenylalkyl;
$R^{10}$ is $R^9$, H, or $-(C=O)R^{11}$ or two $R^{10}$ groups joined to the same nitrogen may form a ring of 5 or 6 members containing up to two heteroatoms chosen from O, S, or N;
$R^{11}$ is H, $C_1$–$C_6$ alkyl, $C_2$–$C_6$ alkenyl, $C_2$–$C_6$ alkynyl, $CF_3$, unsubstituted phenyl, or unsubstituted $C_1$–$C_6$ phenylalkyl;
$R^{12}$ is $-(CH_2)_s-C(R^{13}R^{13})-(CH_2)_s-R^{14}$ or $-CH_2CONR^{10}R^{10}$;
$R^{13}$ is H or $C_1$–$C_4$ alkyl;
$R^{14}$ is a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or the prodrug esters of E (i.e., when $E=-COOR^{12}$) are intended to include the esters such as are described by Saari et al., J. Med. Chem., 21, No. 8, 746-753 (1978), Sakamoto et al., Chem. Pharm. Bull., 32, No. 6, 2241-2248 (1984) and Bundgaard et al., J. Med. Chem., 30, No. 3, 451-454 (1987);
$R^{15}$ is $C_1$ to $C_3$ alkyl, halogen, $CF_3$, $N_3$, $C_1$ to $C_3$ alkoxy, $C_1$ to $C_3$ alkylthio, or $C_1$ to $C_3$ alkylcarbonyl;
$R^{16}$ is H or $R^{15}$;
$R^{17}$ is $R^7$ or HET;
$R^{18}$ is $R^5$, lower alkenyl, lower alkynyl, substituted phenyl-lower alkyl, halo-lower alkyl, halo-lower alkenyl, or halo-lower alkynyl;
and the pharmaceutically acceptable salts thereof.

A preferred group of compounds are those which form special embodiments by this invention and include those compounds described by Formula Ia.

wherein the substituents are as described for Formula I.

A preferred embodiment of Formula Ia is that in which one of the $R^{16}$ substituents is replaced by $R^{15}$.

Some of the compounds described herein contain one or more asymmetric centers and may thus give rise to diastereoisomers and optical isomers. The present invention is meant to comprehend such possible diastereoisomers as well as their racemic and resolved, enantiomerically pure forms and pharmaceutically acceptable salts thereof. Optically active (R) and (S) isomers may be resolved using conventional techniques.

Alkyl, alkenyl, and alkynyl are intended to include linear, branched, and cyclic structures and combinations thereof.

As used herein, the term "alkyl" includes "lower alkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, cyclododecyl, adamantyl, and the like.

As used herein, the term "lower alkyl" includes those alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

As used herein, the term "cycloalkyl" refers to cyclic hydrocarbon rings containing from 3 to 7 carbon atoms.

"Alkenyl" groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl and the like.

As used herein, the term "alkoxy" included those alkoxy groups of from 1 to 6 carbon atoms of either a straight, branched, or cyclic configuration. Examples of alkoxy groups include methoxy, ethoxy, propoxy, isopropoxy, cyclopropyloxy, cyclohexyloxy, and the like.

The terms "substituted phenyl", "substituted benzyl" or "substituted phenethyl" means that the benzene ring in each case carries 1 or 2 $R^{15}$ substitutents.

Halogen includes F, Cl, Br, and I.

It is intended that $R^1$ or $R^2$ may be located in any of positions 3–8 of the quinoline moiety.

It is intended that the definitions of any substituent (e.g., $R^1$, $R^2$, m, E, Z, etc.) in a particular molecule be independent of its definitions elsewhere in the molecule. Thus, $-NR^{10}R^{10}$ represents $-NHH$, $-NHCH_3$, $-NHC_6H_5$, etc.

The heterocycles formed when two $R^{10}$ groups join through N include pyrrolidine, piperidine, morpholine, thiamorpholine, piperazine, and N-methylpiperazine.

The rings formed when two $R^6$ groups join include cyclopropane, cyclobutane, cyclopentane, and cyclohexane.

The pharmaceutical compositions of the present invention comprise a compound of Formula I as an active ingredient or a pharmaceutically acceptable salt, thereof, any may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof. NSAID's which are within the scope of this invention are those disclosed in U.S. Pat. No. 4,683,325 (Jul. 28, 1987)

The following NSAIDs may be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used: 480156S, AA861, AD1590, AFP802, AFP860, AI77B, AP504, AU8001,BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as A-fluoromethylhistidine, described in U.S. Pat. No. 4,325,961. The compounds of the Formula I may also be advantageously combined with an $H_1$ or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126-131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Compounds of Formula I can be tested using the following assays to determine their mammalian leukotriene biosynthesis inhibiting activity.

RAT PERTITONEAL POLYMORPHONUCLEAR (PMN) LEUKOCYTE ASSAY

Rats under ether anesthesia are injected (i.p.) with 8 ml of a suspension of sodium caseinate (6 grams in ca. 50 mL water). After 15-24 hr. the rats are sacrificed ($CO_2$) and the cells from the peritoneal cavity are recovered by lavage with 20 mL of buffer (Eagles MEM containing 30 mM HEPES adjusted to pH 7.4 with NaOH). The cells are pelleted (350 x g, 5 min.), resuspended in buffer with vigorous shaking, filtered, through lens paper, recentrifuged and finally suspended in buffer at a concentration of 10 cells/mL. A 500 µL aliquot of PMN suspension and test compound are preincubated for 2 minutes at 37° C., followed by the addition of 10 µM A-23187. The suspension is stirred for an additional 4 minutes then bioassayed for $LTB_4$ content by adding an aliquot to a second 500 µL portion of the PMN at 37° C. The $LTB_4$ produced in the first incubation causes aggregation of the second PMN, which is measured as a change in light transmission. The size of the assay aliquot is chosen to give a submaximal transmission change (usually —70%) for the untreated control. The percentage inhibition of $LTB_4$ formation is calculated from the ratio of transmission change in the sample to the transmission change in the compound-free control.

HUMAN POLYMORPHONUCLEAR (PMN) LEUKOCYTE $LTB_4$ ASSAY

A. Preparation of Human PMN

Human blood was obtained by antecubital venepuncture from consenting volunteers who had not taken medication within the previous 7 days. The blood was immediately added to 10% (v/v) trisodium citrate (0.13M) or 5% (v/v) sodium heparin (1000 IU/mL). PMNs were isolated from anticoagulated blood by dextran sedimentation of erythrocytes followed by centrifugation through Ficoll-Hypaque (specific gravity 1.077), as described by Boyum.[1] Contaminating erythrocytes were removed by lysis following exposure to ammonium chloride (0.16M) in Tris buffer (pH 7.65), and the PMNs resuspended at $5 \times 10^5$ cells/mL in HEPES (15 mM)-buffered Hanks balanced salt solution containing $Ca^{2+}$ (1.4 mM) and $Mg^{2+}$ (0.7 mM), pH 7.4. Viability was assessed by Trypan blue exclusion and was typically greater than 98%.

(1) Boyum, A. Scand. J. Clin. Lab. Invest. 1968, 21 (Supp 97), 77.

B. Generation and Radioimmunoassay of $LTB_4$

PMNs (0.5 mL; $2.5 \times 10^5$ cells) were placed in plastic tubes and incubated (37° C., 2 min) with test compounds at the desired concentration or vehicle (DMSO, final concentration 0.2%) as control. The synthesis of $LTB_4$ was initiated by the addition of calcium ionophore A23187 (final concentration 10 µM) or vehicle in control samples and allowed to proceed for 5 minutes at 37° C. The reactions were then terminated by the addition of cold methanol (0.25 mL) and samples of the entire PMN reaction mixture were removed for radioimmunoassay of $LTB_4$.

Samples (50 µL) of authentic $LTB_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer were added to reaction tubes. Thereafter [$^3$H]-$LTB_4$ (10 nCi in 100 µL RIA buffer) and $LTB_4$-antiserum (100 µL of a 1:3000 dilution in RIA buffer) were added and the tubes vortexed. Reactants were allowed to equilibrate by incubation overnight at 4° C. To separate antibody-bound from free $LTB_4$, aliquots (50 µL) of activated charcoal (3% activated charcoal in RIA buffer containing 0.25% Dextran T-70) were added, the tubes vortexed, and allowed to stand at room temperature for 10 minutes prior to centrifugation ($1500 \times g$; 10 min; 4° C.). The supernatants containing antibody-bound $LTB_4$ were decanted into vials and Aquasol 2 (4 mL) was added. Radioactivity was quantified by liquid scintillation spectrometry. Preliminary studies established that the amount of methanol carried into the radioimmunoassay did not influence the resuluts. The specificity of the antiserum and the sensitivity of the procedure have been described by Rokach et al.[2] The amounts of $LTB_4$ produced in test and control (approx. 20 ng/$10^6$ cells) samples were calculated. Inhibitory dose-response curves were constructed using a four-parameter algorithm and from these the $IC_{50}$ values were determined.

(2) Rokach, J.; Hayes, E. C.; Girard, Y.; Lombardo, D. L.; Maycock, A. L.; Rosenthal, A. S.; Young, R. N.; Zamboni, R.; Zweerink, H. J. Prostaglandins Leukotrienes and Medicine 1984, 13, 21.

ASTHMATIC RAT ASSAY

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate was supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 μgm/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

The ability of the compounds of Formula I to inhibit biosynthesis of the leukotrienes makes them useful for inhibiting the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary conditions including diseases such as asthma, 2) allergies and allergic reactions such as allergic rhinitis, contact dermatitis, allergic conjunctivitis, and the like, 3) inflammation such as arthritis or inflammatory bowel disease, 4) pain, 5) skin conditions such as psoriasis and the like, and 6) cardiovascular conditions such as angina, endotoxin shock, and the like, and that the compounds are cytoprotective agents.

The cytoprotective activity of a compound may be observed in both animals and man by noting the increased resistance of the gastrointestinal mucosa to the noxious effects of strong irritants, for example, the ulcerogenic effcts of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 10 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001-1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be coadministration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (opthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

Table I illustrates compounds representative of the present invention.

TABLE I

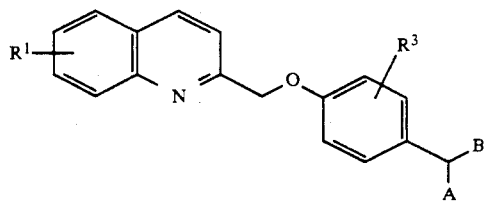

Ib

| Example | R¹ | A | B | R³ |
|---|---|---|---|---|
| 1 | H | —(CH₂)₃Ph | —SCH₂C(O)OH | H |
| 2 | H | —(CH₂)₃Ph | —S(CH₂)₂C(O)OH | H |
| 3 | H | —(CH₂)₃Ph | —SCH₂C(O)OCH₃ | H |
| 4 | H | —(CH₂)₂Ph | —SCH₂C(O)OH | H |
| 5 | H | —(CH₂)₃Ph | —S(CH₂)₂C(O)NH₂ | H |
| 6 | H | —(CH₂)₃Ph | —S(CH₂)₂C(O)N(CH₃)₂ | H |
| 7 | H | —(CH₂)₃Ph | —SCH₂C(CH₃)₂C(O)OH | H |
| 8 | H | —(CH₂)₃Ph | —SC(CH₃)₂CH₂C(O)OH | H |
| 9 | 7-F | —(CH₂)₃Ph | —SCH₂C(O)OCH₃ | H |
| 10 | 7-F | —(CH₂)₃Ph | —SCH₂C(O)OH | H |
| 11 | 5-CF₃ | —(CH₂)₃Ph | —SCH₂C(O)OH | H |
| 12 | H | —(CH₂)₃C₆H₄-4-Cl | —SCH₂C(O)OH | H |
| 13 | H | —(CH₂)₄Ph | —SCH₂C(O)OH | H |
| 14 | H | —(CH₂)₃Ph | —SCH₂C(O)OH | 3-I |
| 15 | H | —(CH₂)₃Ph | —O(CH₂)₂C(O)OH | H |
| 15 | H | —(CH₂)₃Ph | —O(CH₂)₃C(O)OH | H |
| 16 | 4-CH₃ | —(CH₂)₃Ph | —SCH₂C(O)OH | H |
| 16 | 6-CH₃ | —(CH₂)₃Ph | —SCH₂C(O)OH | H |
| 16 | 8-CH₃ | —(CH₂)₃Ph | —SCH₂C(O)OH | H |
| 16 | 6-CF₃ | —(CH₂)₃Ph | —SCH₂C(O)OH | H |
| 16 | 6-CH(CH₃)₂ | —(CH₂)₃Ph | —SCH₂C(O)OH | |
| 16 | 6-OCH₃ | —(CH₂)₃Ph | —SCH₂C(O)OH | H |
| 16 | 7-Cl | —(CH₂)₃Ph | —SCH₂C(O)OH | H |
| 16 | 6-F | —(CH₂)₃Ph | —SCH₂C(O)OH | H |
| 17 | H | —(CH₂)₃C₆H₄-4-Cl | —SCH₂C(O)OH | H |
| 17 | H | —(CH₂)₃C₆H₄-2-Cl | —SCH₂C(O)OH | H |
| 17 | H | —(CH₂)₃C₆H₄-3-Cl | —SCH₂C(O)OH | H |
| 17 | H | —(CH₂)₃C₆H₄-4-SCH₃ | —SCH₂C(O)OH | H |
| 17 | H | —(CH₂)₃C₆H₄-4-Br | —SCH₂C(O)OH | H |
| 17 | H | —(CH₂)₃C₆H₄-4-F | —SCH₂C(O)OH | H |
| 17 | H | —(CH₂)₃C₆H₄-4-CH₃ | —SCH₂C(O)OH | H |
| 17 | H | —(CH₂)₃C₆H₄-4-I | —SCH₂C(O)OH | H |
| 17 | H | —(CH₂)₃C₆H₄-4-OCH₃ | —SCH₂C(O)OH | H |
| 18 | H | —(CH₂)₃C₆H₄-4-CF₃ | —SCH₂C(O)OH | H |
| 18 | H | —(CH₂)₃C₆H₄-4-SCH₃ | —SCH(CH₃)C(O)OH | H |
| 18 | H | —(CH₂)₃C₆H₄-4-F | —S(CH₂)₂C(O)OH | H |
| 18 | H | —(CH₂)₃C₆H₄-4-SCH₃ | —S(CH₂)₂C(O)OH | H |
| 18 | H | —(CH₂)₃C₆H₄-4-Br | —S(CH₂)₂C(O)OH | H |
| 18 | H | —(CH₂)₃C₆H₄-4-Cl | —S(CH₂)₂C(O)OH | H |
| 18 | H | —(CH₂)₃C₆H₄-4-CF₃ | —OCH₂C(O)OH | H |
| 18 | H | —(CH₂)₃C₆H₄-4-F | —OCH₂C(O)OH | H |
| 18 | H | —(CH₂)₃C₆H₄-4-SCH₃ | —OCH₂C(O)OH | H |
| 18 | H | —(CH₂)₃C₆H₄-4-Br | —OCH₂C(O)OH | H |
| 18 | H | —(CH₂)₃C₆H₄-4-CF₃ | —O(CH₂)₂C(O)OH | H |
| 18 | H | —(CH₂)₃C₆H₄-4-F | —O(CH₂)₂C(O)OH | H |
| 18 | H | —(CH₂)₃C₆H₄-4-SCH₃ | —O(CH₂)₂C(O)OH | H |
| 18 | H | —(CH₂)₃C₆H₄-4-Br | —O(CH₂)₂C(O)OH | H |
| 18 | H | —(CH₂)₃C₆H₄-4-Cl | —O(CH₂)₂C(O)OH | H |
| 18 | H | —(CH₂)₃C₆H₄-4-Cl | —OCH₂C(O)OH | H |
| 18 | 6-CH(CH₃)₂ | —(CH₂)₃Ph | —S(CH₂)₂C(O)OH | H |
| 18 | 6-OCH₃ | —(CH₂)₃Ph | —SCH₂C(O)OH | H |
| 18 | 6-OCH₃ | —(CH₂)₃Ph | —S(CH₂)₂C(O)OH | H |
| 18 | 6-F | —(CH₂)₃Ph | —SCH₂C(O)OH | H |
| 19 | H | —(CH₂)₂Ph | —(CH₂)₃C(O)OH | H |
| 19 | H | —(CH₂)₃Ph | —(CH₂)₃C(O)OH | H |
| 19 | H | —(CH₂)₃Ph | —(CH₂)₂C(CH₃)₂C(O)OH | H |
| 20 | H | —(CH₂)₃—C₆H₄-4-N₃ | —S(CH₂)₂C(O)N(CH₃)₂ | H |
|  | 7-CH=CH₂ | —(CH₂)₃—C₆H₄-2-COCH₃ | —S—(CH₂)₂C(O)OH | 2-CF₃ |
|  | 6-C≡C—CH₃ | —(CH₂)₃Ph | —S—(CH₂)₂C(O)OH | 3-CH₃ |
|  | 5-S—CH₃ | —(CH₂)₃—C₆H₄-3-C₂H₅ | —S—(CH₂)₂C(O)OH | 3-OCH₃ |
|  | 5-S(O)CH₃ | —(CH₂)₃Ph | —S—(CH₂)₂C(O)OH | 3-CF₃ |
|  | 5-S(O)₂CH₃ | —(CH₂)₃—C₆H₄-3-OC₂H₅ | —S—(CH₂)₂C(O)OH | 2-CN |
|  | 7-N(CH₃)₂ | —(CH₂)₃Ph | —S—(CH₂)₂C(O)OH | 2-N₃ |
|  | 8-CHO | —(CH₂)₃Ph | —S—(CH₂)₂C(O)OH | 3-OCH₃ |
|  | 7-C(O)CH₃ | —(CH₂)₃—C₆H₄-3-S-n-C₃H₇ | —S—(CH₂)₂C(O)OH | 3-CF₃ |
|  | 7-CH(OH)CH₃ | —(CH₂)₃Ph | —S—(CH₂)₂C(O)OH | 2-SCH₃ |
|  | 6-CN | —(CH₂)₃Ph | —S—(CH₂)₂C(O)OH | 2-S(O)CH₃ |
|  | 6-NO₂ | —(CH₂)₃Ph | —S—(CH₂)₂C(O)OH | 2-C(O)OC₂H₅ |
|  | 6-N₃ | —(CH₂)₃Ph | —S—(CH₂)₂C(O)OH | 2-CH=CH₂ |

TABLE I-continued

Ib

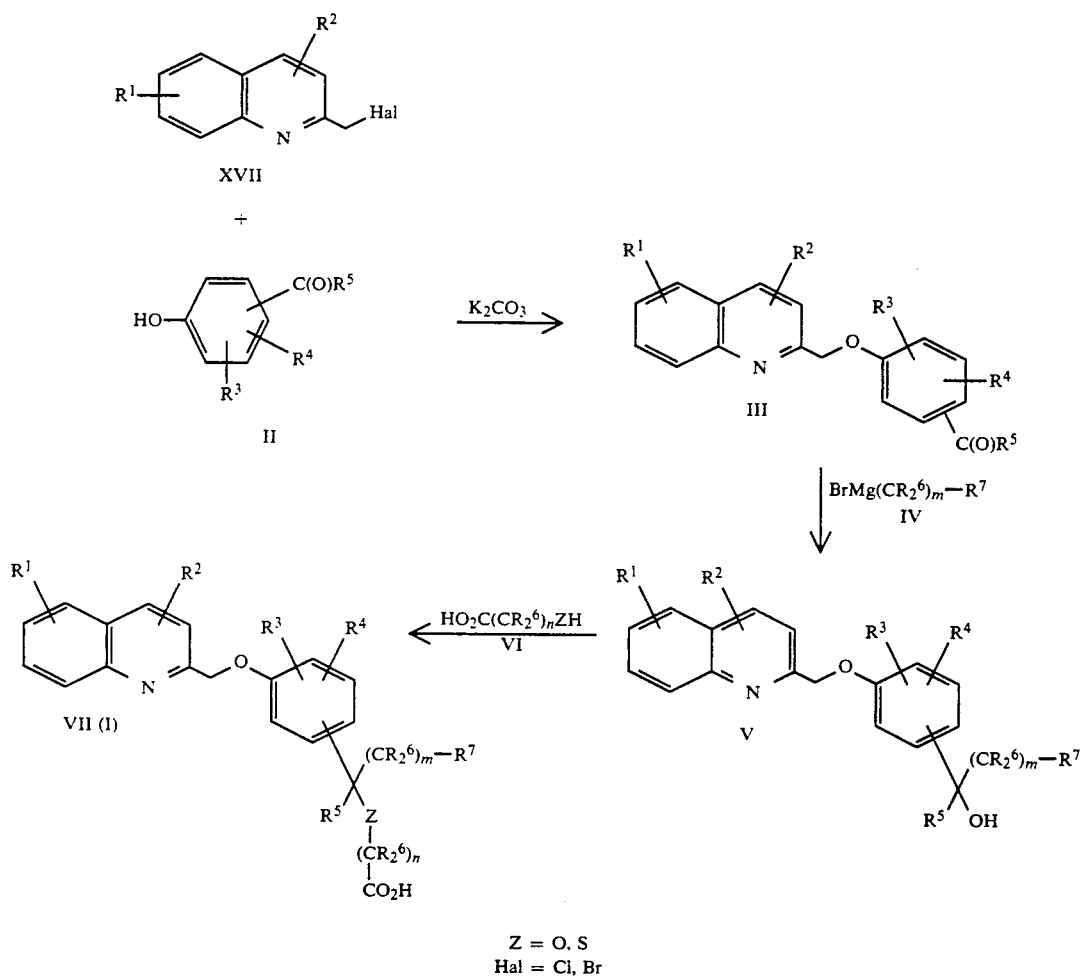

| Example | R¹ | A | B | R³ |
|---|---|---|---|---|
| | H | —(CH₂)₃Ph | —S—(CH₂)₂C(O)OH | 2-S(O)₂N(CH₃)₂ |

Compounds of the present invention can be prepared according to the following methods. Temperatures are in degree Celsius.

$Z = O, S$
$Hal = Cl, Br$

METHOD A 2-(halogenomethyl)quinoline derivative XVII is condensed with carbonyl compound II in the presence of a suitable base to give the adduct III. The aldehyde III is reacted with an organometallic reagent IV in a suitable solvent to afford the alcohol V. Alcohol V is reacted with acid VI in the presence of a Lewis acid such as BF₃·OEt₂ or ZnI₂ to provide VII. Or alternatively, the alcohol V is reacted with the ester IX in the presence of a Lewis acid and the resultant ester is hydrolysed with aqueous base such as sodium hydroxide, to afford VII.

METHOD B

Alternatively, the aldehyde II is first reacted with the organometallic reagent IV to afford the alcohol VIII. Treatment of the alcohol VIII with ester IX in the presence of a Lewis acid such as BF₃·OEt₂ provides the adduct X. Condensation of X with 2-(halogenomethyl)quinoline derivative XVII in the presence of a suitable base such as K₂CO₃ and hydrolysis of the resultant product with aqueous base such as sodium hydroxide provides VII.

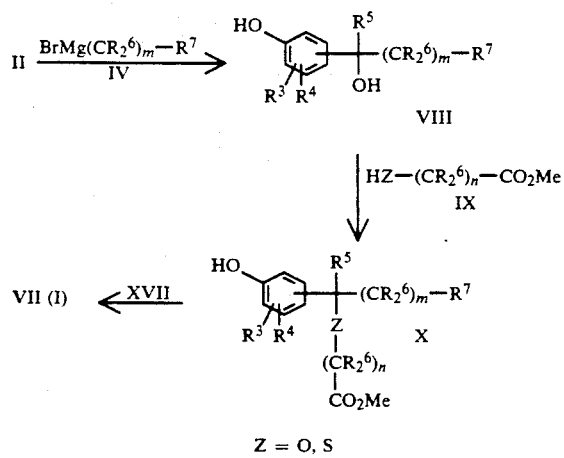

METHOD C

Alternatively, the substituted aldehyde XI is reacted with the Wittig reagent XII to afford the olefin XIII. Hydrogenation of the olefin using a suitable catalyst such as palladium on carbon in an appropriate solvent gives the corresponding alkane which is deprotected using a two step procedure by an acetal exchange using p-toluene sulfonic acid in methanol followed by treatment of the resultant dimethoxy acetal with aqueous acetic acid to give the aldehyde XIV. Reaction of the aldehyde XIV with the Grignard reagent XVI provides the phenol XV after deprotection with $Bu_4NF$. Condensation of the phenol XV with 2-(halogenomethyl)-quinoline XVII in the presence of an appropriate base gives the adduct V which can be coupled with VI (or IX) as in Method A to give product XVI.

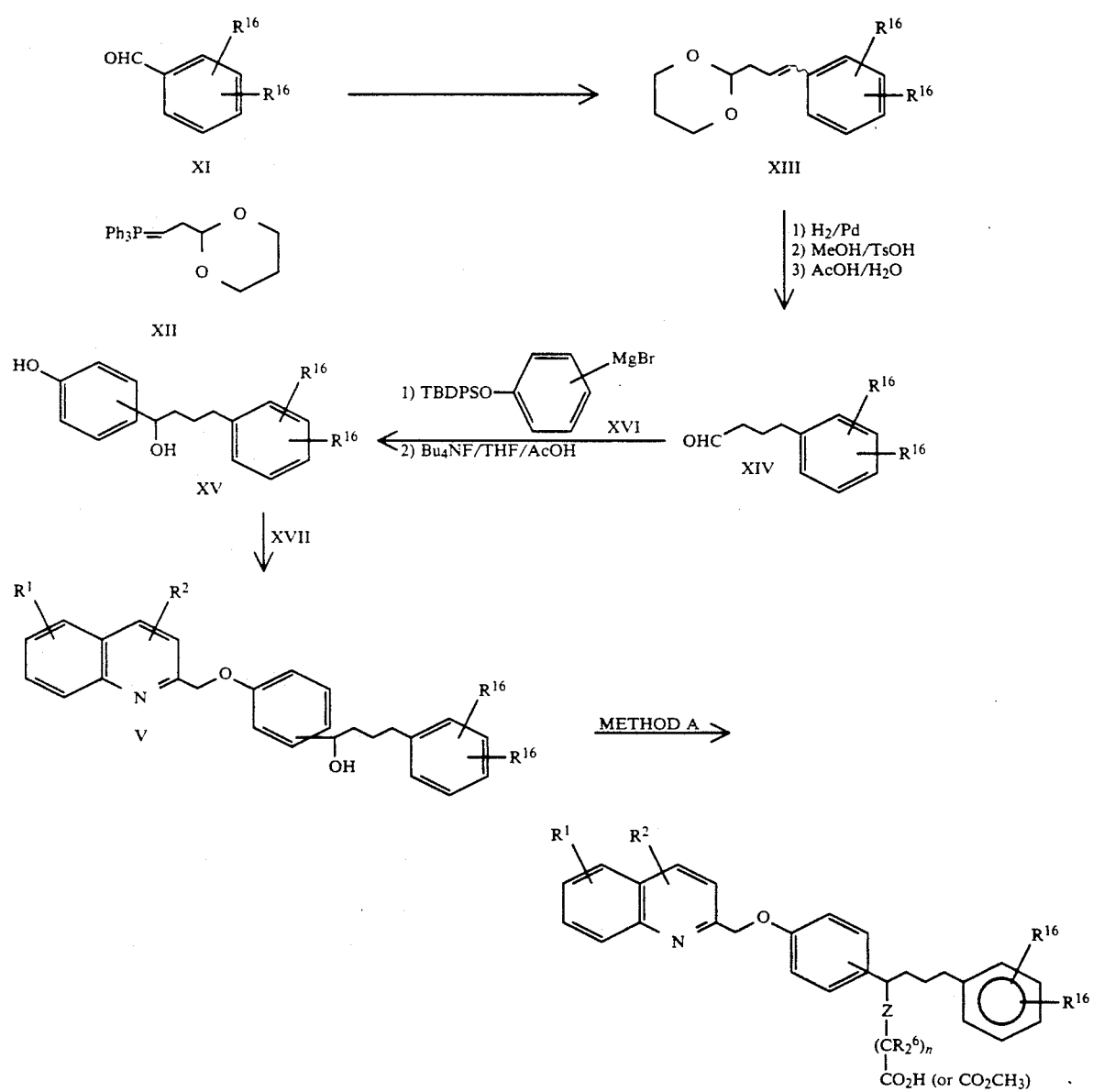

METHOD D
For compounds in which Z is CH$_2$ the following scheme may be employed:
Table II illustrates compounds representative of the present invention.
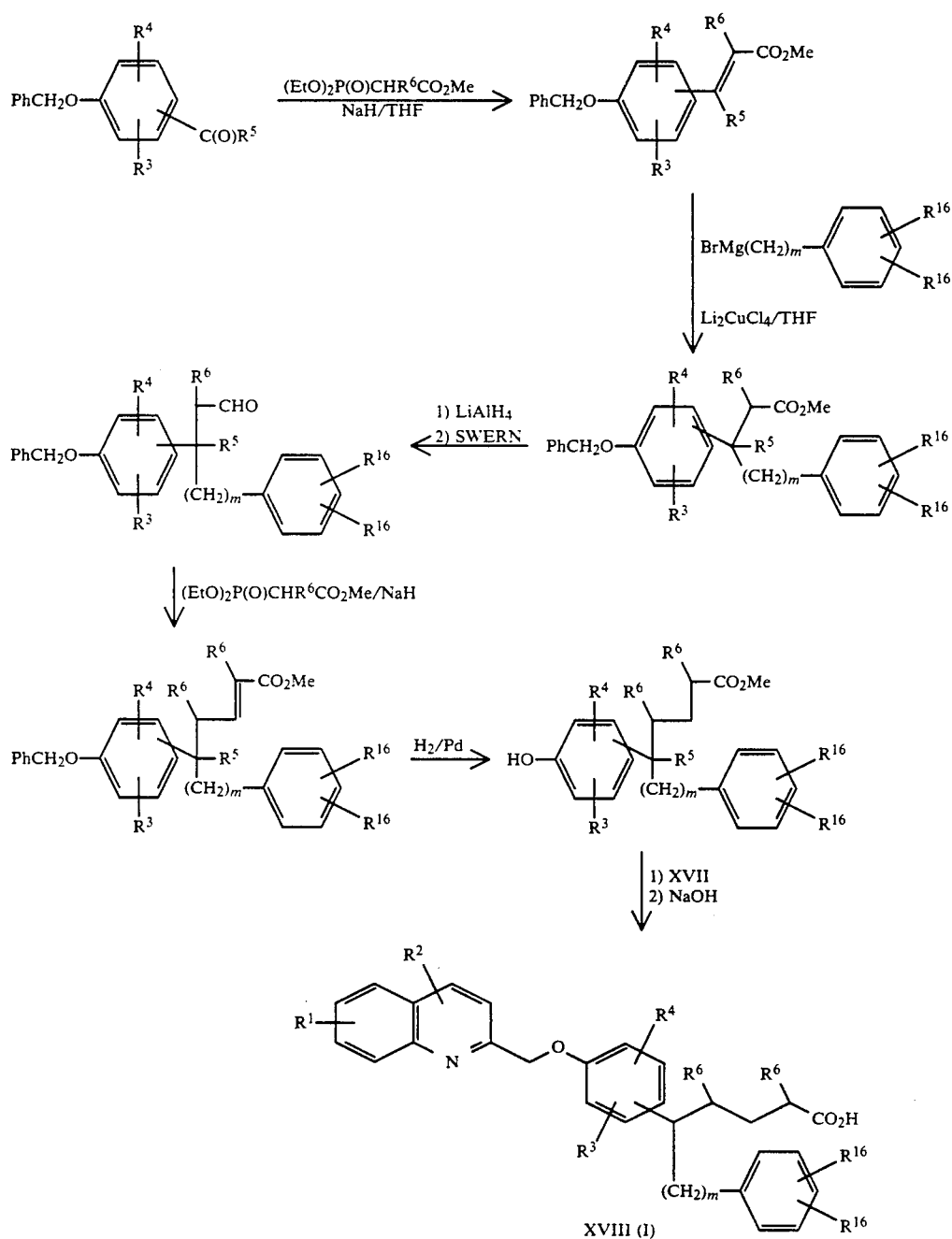
XVIII (I)

TABLE II

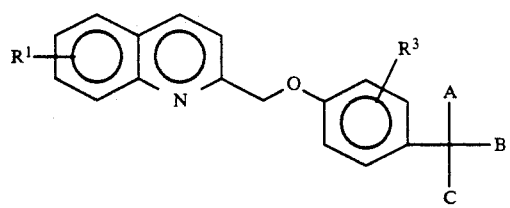

Ic

| EXAMPLE | R¹ | A | B | C | R³ |
|---|---|---|---|---|---|
| 21 | H | H | —CH₂OCH₂Ph | —SCH₂CO₂H | H |
| 22 | H | H | —CH₂OCH₂Ph-4-Cl | —SCH₂CO₂H | H |
| 23 | H | H | —CH₂OCH₂Ph-4-CF₃ | —SCH₂CO₂H | H |
| 24 | H | H | —(CH₂)₃Ph-4-Cl | —OCH₂CO₂H | H |
| 25 | H | —CH₂Ph-4-Cl | —(CH₂)₃Ph-4-Cl | —SCH₂CO₂H | H |
| 26 | H | —CH₂Ph-4-Cl | —(CH₂)₃Ph-4-Cl | —S(CH₂)₂CO₂H | H |
| 27 | H | —CH₂Ph-4-Cl | —(CH₂)₃Ph-4-Cl | —SCH₂C(CH₃)₂CO₂H | H |
| 28 | H | —CH₂Ph-4-Cl | —(CH₂)₃Ph-4-Cl | —SCH(CH₃)CO₂H | H |
| 29 | H | —CH₂Ph-4-Cl | —(CH₂)₃Ph-4-Cl | —S(CH₂)₃CO₂H | H |
| 30 | H | —CH₂CHCH₂ | —(CH₂)₃Ph-4-Cl | —SCH₂CO₂H | H |
| 31 | H | —CH₃ | —(CH₂)₃Ph-4-Cl | —SCH₂CO₂H | H |
| 32 | H | —(CH₂)₃Ph | —(CH₂)₃Ph | —SCH₂CO₂H | H |
| 33 | H | —CH₂Ph | —(CH₂)₃Ph | —SCH₂CO₂H | H |
| 34 | H | —(CH₂)₂Ph | —(CH₂)₃Ph | —SCH₂CO₂H | H |
| 35 | H | H | —SCH₂Ph-4-Cl | —SCH₂CO₂H | H |
| 36 | H | H | —S-4-Pyr | —SCH₂CO₂H | H |
| 37 | H | H | —SCH₂Ph | —SCH₂CO₂H | H |
| 38 | H | H | —S(CH₂)₂Ph | —SCH₂CO₂H | H |
| 39 | H | —CH₂Ph | —(CH₂)₃Ph | —S(CH₂)₂CO₂H | H |
| 40 | H | —(CH₂)₂Ph | —(CH₂)₃Ph | —S(CH₂)₂CO₂H | H |
| 41 | H | —CH₂CHCH₂ | —(CH₂)₃Ph-4-Cl | —S(CH₂)₂CO₂H | H |
| 42 | 7-Cl | —CH₂Ph | —(CH₂)₃Ph | —S(CH₂)₂CO₂H | H |
| 43 | 6-CF₃ | —CH₂Ph | —(CH₂)₃Ph | —S(CH₂)₂CO₂H | H |
| 44 | H | —CH₂Ph | —(CH₂)₃Ph | —S(CH₂)₂CO₂H | 2-Cl |
| 45 | 6-MeO | —CH₂Ph | —(CH₂)₃Ph | —SCH₂CO₂H | H |
| 46 | 5-Br | —CH₂Ph | —(CH₂)₃Ph | —SCH₂CO₂H | H |
| 47 | H | —C₂H₅ | —(CH₂)₃Ph-4-Cl | —SCH₂CO₂H | H |
| 48 | H | -n-C₃H₇ | —(CH₂)₃Ph-4-Cl | —S(CH₂)₂CO₂H | H |
| 49 | H | —(CH₂)₃CF₃ | —(CH₂)₃Ph-4-Cl | —S(CH₂)₂CO₂H | H |
| 50 | H | —(CH₂)₃CF₃ | —(CH₂)₅CF₃ | —S(CH₂)₂CO₂H | H |
| 51 | H | —CH₂CCH | —(CH₂)₃Ph | —SCH₂CO₂H | H |
| 52 | H | —CCH | —(CH₂)₃Ph | —SCH₂CO₂H | H |
| 53 | H | —CCH | —(CH₂)₃Ph | —SCH₂CO₂H | 3-S(O)₂CH₃ |
| 54 | H | —CH₂CHCCl₂ | —(CH₂)₃Ph-4Cl | —SCH₂CO₂H | H |
| 55 | H | —CH₂CF₃ | —(CH₂)₃Ph-4Cl | —SCH₂CO₂H | H |
| 56 | 7-CN | —(CH₂)₃CH₂Cl | —(CH₂)₃Ph-4Cl | —SCH₂CO₂H | H |

METHOD E

The alcohol V is oxidised with manganese dioxide to provie the ketone XIX. The ketone XIX is reacted with an organometallic reagent in a suitable solvent to afford alcohol XX. Alcohol XX is reacted with acid VI in the presence of a Lewis acid such as $BF_3.OEt_2$ to provide XXI. Alternatively, the alcohol XX is reacted with the ester IX in the presence of a Lewis acid and the resultant ester is hydrolysed with aqueous base such as sodium hydroxide to afford the acid XXI.

METHOD F 2-(Halogenomethyl)quinoline derivative XVII is condensed with the phenol XXII in the presence of a suitable base to give the adduct XXIII. The diol XXIII is coupled with benzyl halide in the presence of a suitable base to give the adduct XXIV. The ether XXIV is reacted with acid VI in the presence of a Lewis acid such as $BF_3.OEt_2$ to proide XXV. Alternatively, the ether is reacted with the ester IX in the presence of a Lewis acid and the resultant ester is hydrolysed with aqueous base such as sodium hydroxide.

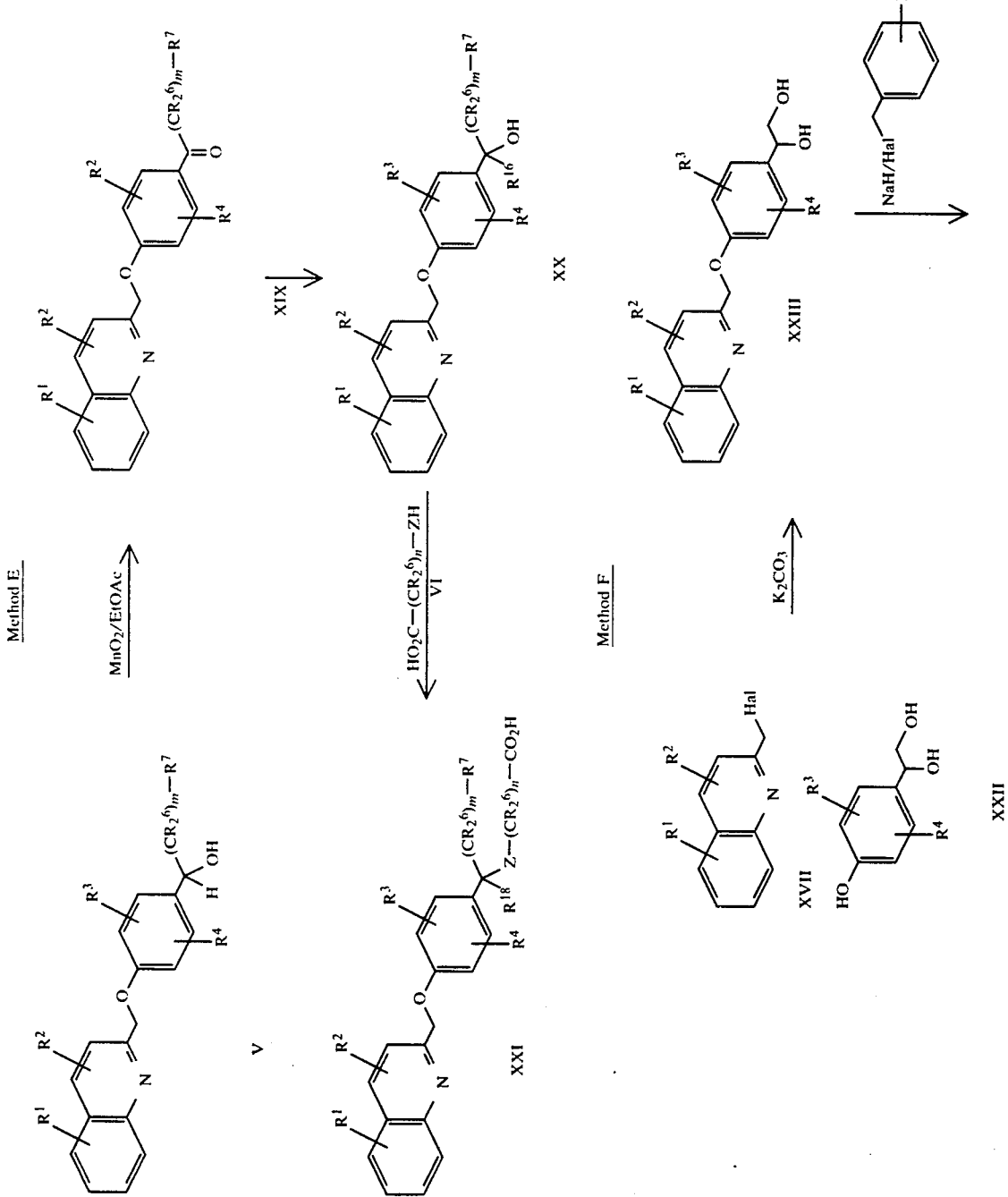

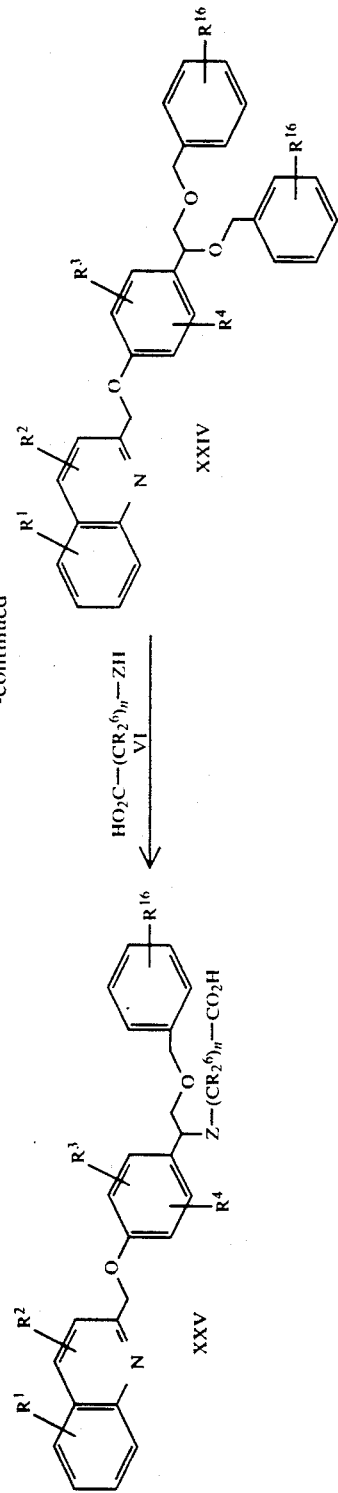

The invention is further defined by reference to the following examples, which are intended to be illustrative and not limiting. All temperatures are in degrees Celsius. All NMR spectra were recorded in deuterochloroform except where otherwise noted; chemical shifts are reported in ppm from tetramethylsilane.

EXAMPLE 1

{[4-phenyl-1-(4-(2-quinolinylmethoxy)phenyl)butyl]thio}acetic acid

Step I: Preparation of 4-(2-quinolinylmethoxy)benzaldehyde

A mixture containing 2-(chloromethyl)quinoline hydrochloride (15 g), 4-hydroxybenzaldehyde (8.56 g) and anhydrous potassium carbonate (29 g) was heated under reflux in acetone (300 mL) for 86 h. After cooling to room temperature, ether (400 mL) was added and the mixture was filtered on celite. The filtrate was evaporated to dryness under reduced pressure and purified by flash chromatography using 15% ethyl acetate/hexane. The title compound was obtained after recrystallization from ethyl acetate/hexane m.p. 89°-90°.

Step II: Preparation of 4-phenyl-4-(4-(2-quinolinylmethoxy)phenyl)butanol

To a suspension of magnesium turnings (3.47 g) in ether (30 mL) was added a small amount of a solution of 1-bromo-3-phenylpropane (28.6 g) in ether (20 mL). The reaction was initiated by the addition of dibromoethane (100 μL). Once the reaction started, the reaction was kept at a gentle reflux by controlling the rate of the addition of the bromide. When the addition was over, the mixture was heated for a further hour at 40°. After cooling, the concentration of the organometallic was determined by titration with methol in THF using 1,10-phenanthroine as an indicator.

To a solution of the aldehyde from Step I, (1.34 g) in THF at 0° was added dropwise the 3-phenylpropylmagnesium bromide (1.1 mol. equiv., from above). After 30 mins, the reaction was quenched by the addition of 25% aqueous NH$_4$OAc solution. The mixture was then extracted with ethyl acetate (x2), the organic phase was washed with brine (x2), dried and evaporated under reduced pressure. The title compound was obtained after recrystallization from ethyl acetate/hexane, m.p. 118°-119°.

Step III: {[4-phenyl-1-(4-(2-quinolinylmethoxy)phenyl)butyl]thio}acetic acid, methyl ester To a mixture of the alcohol (1.56 g) (Step II) and methyl thioglycolate (414 μL) in dichloromethane (20 mL) at 0° was added BF$_3$.OEt$_2$ (1.10 mL) dropwise. The mixture was stirred at 0° for 1 h and poured onto buffer (pH 7), extracted with dichloromethane and the organic phase was dried and evaporated. Flash chromatography using 20% ethyl acetate/hexane afforded the title compound as a syrup.

$^1$H NMR: 8.3-6.9 (m, 15H), 5.37 (s, 2H), 3.94 (dd, 1H, J=10,7), 3.66 (s, 3H), 3.00 (d, 1H, J=15), 2.86 (d, 1H, J=15), 2.58 (t, 2H, J=6), 1.98-1.74 (m, 2H), 1.74-1.40 (m, 2H).

Step IV

To a solution of the ester (Step III) in 20 mL of THF/MeOH (1:1) was added NaOH (6 mL, 1M). After 1 h at RT, the reaction was acidified with aqueous citric acid and the organic phase was partially evaporated. The solid was filtered off, washed with water and recrystallized from ethyl acetate/hexane to afford the title compound. m.p. 141°-143°.

EXAMPLE 2

3-{[4-phenyl-1-(4-(2-quinolinylmethoxy)phenyl)butyl]thio]propanoic acid

Using the procedure of Example 1 but replacing methyl thioglycolate with methyl 3-mercaptopropionate in Step III, there was obtained the title compound. m.p. 97°-100°.

EXAMPLE 3

{[4-phenyl-1-(4-(2-quinolinylmethoxy)phenyl)butyl]thio}acetic acid, methyl ester Using the procedure of Example 1 but omitting Step IV there was obtained the title compound a syrup.

$^1$H NMR: 8.3-6.9 (m, 15H), 5.37 (s, 2H), 3.94 (dd, 1H, J=10, 7), 3.66 (s, 3H), 3.0 (d, 1H, J=15), 2.86 (d, 1H, J=15), 2.58 (t, 2H, J=6), 1.98-1.74 (m, 2H), 1.74-1.40 (m, 2H).

EXAMPLE 4

{[3-phenyl-1-(4-(2-quinolinylmethoxy)phenyl)propyl]thio}acetic acid

Step I: 1-(4-Hydroxyphenyl)-3-phenyl-1-propanol

To a solution of p-hydroxybenzaldehyde (1.50 g) in THF (30 mL) was added dropwise a solution of 2-phenylethyl magnesium bromide in ether (15.2 mL, 1.7M) at 0°. After being stirred overnight at room temperature (RT) using a mechanical stirrer, it was poured onto a buffer (pH 7), extracted with ethyl acetate and the organic phase was dried and evaporated. The title compound was obtained after crystallization from ethyl acetate/hexane and was used directly in the next step.

Step II: {[1-(4-hydroxyphenyl)-3-phenylpropyl]thio}acetic acid, methyl ester

To a solution of the phenol (441 mg) (Step 1) and methyl thioglycolate (190 μL) in dichloromethan (5 mL) at 0° was added ZnI$_2$ (30 mg). The mixture was stirred at RT for 1 h and poured onto buffer (pH 7), extracted with dichloromethane, and the organic phase was dried and evaporated to give the crude product. This material was used directly in the next step without further purification.

Step III:

The phenol (Step II) was heated in refluxing acetone with 2-(chloromethyl)quinoline (343 mg) in the presence of K$_2$CO$_3$ (293 mg), NaI (0.1 mol equiv) and Cs$_2$CO$_3$ (0.1 mol equiv). After 48 h, the mixture was diluted with CH$_2$Cl$_2$ and was filtered and the filtrate was concentrated. The residue was dissolved in dichloromethane and was washed with water, dried and evaporated. Flash chromatography (10% ethyl acetate/hexane) afforded the ester as an oil.

Step IV:

The ester (Step III) was hydrolysed with NaOH (1.1 mol equiv, 1M) in 1:1 MeOH/THF (5 mL) at RT for 1 h. After acidifying the mixture with aqueous citric acid, the volatile organics were removed and the residue was extracted with ethyl acetate. Recrystallized from ethyl acetate/hexane, the title compound had m.p. 117°-118°.

EXAMPLE 5

3-{[4-phenyl-1-(4-(2-quinolinylmethoxy)phenyl)butyl]thio}propanamide

To a solution of the title acid of Example 2 (200 mg) in CH$_2$Cl$_2$ (3 mL) and CH$_3$CN (1 mL) at 0° C. was added Et$_3$N (120 μL) followed by 2-chloro1-methylpyridinium iodide (220 mg). After stirring for 75 mins. at 0° C., an excess of NH$_3$ was slowly bubbled into the mixture and the reaction was allowed to stir at RT for 12 h. It was then diluted with ethyl acetate and washed successively with aq. NH$_4$OAc (x2) and brine. After drying, the organic solution was concentrated and the residue was purified on a column of silica to afford the title compound.

$^1$H NMR: δ 8.35 (d, 1H, 9 Hz), 8.1-7.0 (m, 14H), 6.6-6.8 (br, 1H, NH), 6.1-6.3 (br, 1H, NH), 5.35 (s, 2H), 3.9 (t, 1H), 2.65-2.25 (m, 6H), 2.0-1.5 (m, 4H).

EXAMPLE 6

N,N-dimethyl-3-{[4-phenyl-1-(4-(2-quinolinylmethoxy)phenyl)butyl]thio}propanamide Using the procedure of Example 1 but replacing methyl thioglycolate with N,N-dimethyl-3-mercaptopropanamide in Step III and omitting the hydrolysis Step IV there was obtained the title compound as a syrup.

$^1$H NMR: 8.20 (d, 1H, J=9), 8.10 (d, 1H, J=9), 8.86-7.50, (m, 4H0, 7.28-7.06 (m, 7H), 6.98 (d, 2H, J=10), 5.37 (s, 2H), 3.76 (dd, 1H, J=6,8), 2.88 (s, 3H), 2.84 (s, 3H), 2.70-2.45 (m, 4H), 2.40-2.30 (m, 2H), 2.0-1.75 (m, 2H), 1.75-1.40 (m, 2H).

EXAMPLE 7

2,2-dimethyl-3-{[4-phenyl-1-(4-(2-quinolinylmethoxy)phenyl)butyl]thio}propanoic acid Using the procedure of Example 1 but replacing methyl thioglycolate with 2,2-dimethyl-3-mercaptopropanoic acid in Step III and omitting the hydrolysis Step IV there was obtained the titled compound as a syrup after chromatography with silica using 30% ethyl acetate/hexane.

$^1$H NMR: δ 8.21 (d, 1H, J=9), 8.12 (d, 1H, J=9), 7.90-7.50 (m, 4H), 7.30-7.0 (m, 7H), 6.95 (d, 2H, J=9), 5.38 (s, 2H), 3.72 (t, 1H, J=10), 2.84 (m, 2H), 2.54 (d, 1H, J=15), 2.43 (d, 1H), J=15), 1.95-1.70 (m, 2H), 1.70-1.40 (m, 2H), 1.19 (s, 3H), 1.16 (s, 3H).

EXAMPLE 8

3,3-dimethyl-3-{[4-phenyl-1-(4-(2-quinolinylmethoxy)phenyl)butyl]thio}propanoic acid Using the procedure of Example 7 but replacing 2,2-dimethyl-3-mercaptopropanoic acid in Step III with 3,3-dimethyl-3-mercaptopropanoic acid there was obtained the title compound after chromatography on silica using 30% ethyl acetate/hexane containing 0.3% acetic acid, m.p. 90°-92°.

EXAMPLE 9

{[1-(4-(7-fluoro-2-quinolinylmethoxy)phenyl)-4-phenylbutyl]thio}acetic acid, methyl ester Using the procedure of Example 4, but replacing 2-phenylethyl magnesium bromide with 3-phenylpropyl magnesium bromide in Step I and 2-(chloromethyl)quinoline with 7-fluoro-2-bromomethyl quinoline in Step III and omitting the hydrolysis (Step IV) there was obtained the title compound after chromatography on silica using 16% ethyl acetate/hexane, m.p. 64°-66°.

EXAMPLE 10

{[1-(4-(7-fluoro-2-quinolinylmethoxy)phenyl)-4-phenylbutyl]thio}acetic acid

Using the procedure of Example 4, Step IV, the title compound of Example 9 was hydrolysed to the title acid m.p. 126°-128°.

EXAMPLE 11

{[4-(phenyl)-1-(4-((5-(trifluoromethyl)-2-quinolinyl)methoxy)phenyl)butyl]thio}acetic acid Using the procedure of Example 1 but replacing 2-(chloromethyl)quinoline with 2-(bromomethyl)-5-trifluoromethylquinoline there was obtained the title compound.

$^1$H NMR: 8.6 (d, 1H), 8.4 (d, 1H), 8.2 (d, 1H), 8.0 (m, 3H), 7.0-7.4 (m, 8H), 5.5 (s, 2H), 4.15 (dd, 1H), 3.5 (dd, 2H), 2.7 (t, 2H), 1.9-2.2 (m, 2H), 1.6-1.9 (m, 2H).

EXAMPLE 12

{[4-(4-chlorophenyl)-1-(4-(2-quinolinylmethoxy)phenyl)butyl]thio}acetic acid

Using the procedure of Example 1 but replacing 3-phenylpropyl bromide with 3-(4-chlorophenyl)propyl bromide there was obtained the title compound.

Calc'd for C$_{28}$H$_{26}$ClNO$_3$S: C 68.35, H 5.33, N 2.84, S 6.51 Cl 7.20. Found C 68.21, H 5.32, N 2.80, S 6.81 Cl 7.12

EXAMPLE 13

{[5-phenyl-1-(4-(2-quinolinylmethoxy)phenyl)pentyl]thio}acetic acid

Using the procedure of Example 1 but replacing 3-phenylpropyl magnesium bromide in Step II with 4-phenylbutyl magnesium bromide there was obtained the title compound as an oil after chromatography on silicic acid.

$^1$H NMR: w 8.24 (d, 1H, J=10), 8.16 (d, 1H, J=10), 7.90-7.70 (m, 3H), 7.56 (t, 1H, J=10), 7.30-7.05 (m, 7H), 6.98 (d, 2H, J=10), 5.20 (s, 2H), 3.99 (dd, 1H, J=9.6), 3.06 (d, 1H, J=15), 2.93 (d, 1H, J=15), 2.52 (t, 2H, J=7), 2.0-1.7 (m, 2H), 1.65-1.48 (m, 2H), 1.48-1.20 (m, 2H).

EXAMPLE 14

{[4-phenyl-1-(3-iodo-4-(2-quinolinylmethoxy)phenyl)butyl]thio}acetic acid

Using the procedure of Example 4 but in Step I 2-phenylethyl magnesium bromide was replaced by 3-phenylpropyl magnesium bromide and 1-(4-hydroxyphenyl)-4-phenyl-1-butanol so obtained was iodinated in the following manner: the phenol from above (205 mg) was dissolved in concentrated NH$_4$OH and cooled to −20° C. and an aqueous solution of KI$_3$ (8.47 mL, 0.1M) was added dropwise. The mixture was then extracted with ethyl acetate (×2) and the organic extract washed successively with a solution of sodium thiosulfate and NH$_4$OAc. The organic phase was dried and concentrated and was used in the Step II without further purification.

The title compound was obtained after purification of silica.

$^1$H NMR: δ 8.29 (d, 1H, J=10), 8.14 (d, 1H, J=10), 7.96 (d, 1H, J=9), 7.90-7.70 (m, 3H), 7.56 (t, 1H, J=6), 7.30-7.0 (m, 6H), 6.86 (d, 1H, J=9), 5.45 (s, 2H), 3.96 (t,

1H, J=7), 3.08 (d, 1H, J=16), 2.94 (d, 1H, J=16), 2.57 (t, 2H, J=7), 2.0–1.75 (m, 2H), 1.75–1.40 (m, 2H).

EXAMPLE 15

When methyl thioglycolate of Example 1 (Step III) is replaced by the hydroxyesters below, and using the appropriate Lewis acid catalysis (S. Kim et al., Journal of Organic Chemistry, 1987, 52, 3917), then the corresponding products are obtained.
Methyl 3-hydroxypropionate
Methyl 4-hydroxybutanoate.

EXAMPLE 16

When 2-(chloromethyl)quinoline of Example 1 (Step 1) is replaced by the quinoline compounds below, the corresponding products are obtained.
2-(chloromethyl)-4-methylquinoline
2-(chloromethyl)-6-methylquinoline
2-(chloromethyl)-8-methylquinoline
2-(bromomethyl)-6-trifluoromethylquinoline
2-(bromomethyl)-6-isopropylquinoline
2-(bromomethyl)-6-methoxyquinoline
2-(bromomethyl)-7-chloroquinoline
2-(bromomethyl)-6-fluoroquinoline.

EXAMPLE 17

{[4-(4-chlorophenyl)-1-(4-(2-quinolinylmethoxy)-phenyl)butyl]thio}acetic acid

Step I: Preparation of 4-(4-chlorophenyl)-3-butene-1-ol

To a suspension of 3-((2-methoxy)-2-propoxy)-propyl)triphenyl phosphonium bromide (4.42 g, 10 mmoles) in THF (100 mL) was added n-BuLi (6 mL of 1.6M) at −78°. The reaction mixture was stirred at −78° for 30 min. 4-Chlorobenzaldehyde (1.4 g, 10 mM) was added and the reaction was warmed to RT. The reaction mixture was quenched with buffer and extracted with ethyl acetate. After evaporation of the ethyl acetate, the crude residue was dissolved in 25 mL THF and 5 mL of AcOH plus 5 mL H$_2$O was added. The mixture was stirred for 2 hours at RT and evaporated. The residue was extracted with ethyl acetate, and the ethyl acetate evaporated. Flash chromatography of the residue using 25% ethyl acetate/hexane afforded the title compound as a mixture of cis and trans isomers.

$^1$H NMR (CD$_3$COCD$_3$): δ 2.4–2.6 (m, 2H), 3.6–3.8 (m, 2H), 5.7–5.8 and 6.15 (m, 2H), 6.4 (dd, 1H), 7.1–7.3 (m, 4H).

Step II: Preparation of 4-(4-chlorophenyl)butanol

To the alcohol (3 g) (Step I) in DMF (50 mL) was added 10% Pd/C (300 mg). Hydrogen was added (balloon) and the mixture was vigorously stirred for 4 hours. The reaction mixture was filtered, H$_2$O was added, the mixture was extracted with ethyl acetate and the organic extracts dried and evaporated. Flash chromatography of the residue using 40% ethyl acetate/hexane afforded the title compound.

$^1$H NMR (CD$_3$COCD$_3$) δ: 1.6–1.8 (m, 4H), 2.55 (t, 2H), 3.6 (m, 2H), 7.05–7.3 (4H).

Step III: Preparation of 4-(4-chlorophenyl)butanal

To a suspension of pyridinium chlorochromate (PCC) (5 g) in CH$_2$Cl$_2$ (200 mL) and 4 angstrom molecule sieves (5 g) was added the alcohol (2 g) (Step II). The mixture was stirred 2 hr at RT, filtered through celite and evaporated. Flash chromatography using 25% ethyl acetate in hexane afforded the title compound.

$^1$H NMR: (CD$_3$COCD$_3$) δ: 1.9 (q, 2H), 2.45 (dt, 2H), 2.65 (t, 2H), 7.25 (q, 4H), 9.8 (s, 1H).

Step IV: Preparation of 4-(t-butyldiphenylsiloxy)-bromobenzene

To a solution of 4-bromophenol (16.4 g, 0.1 mole) in CH$_2$Cl$_2$ (300 mL) was added t-butyldiphenylsilyl chloride (29 g, 0.1 mole), Et$_3$N (20 g, 0.2 mole) and 4-dimethylaminopyridine (DMAP) (1 g). The solution was stirred at RT for 2 days, quenched with H$_2$O (1L) and extracted with ether (2L). The ether extracts were dried and evaporated. Flash chromatography of the residue using 5% ethyl acetate in hexane afforded the title compound which was used as such for the next step.

Step V: Preparation of 4-(4-chlorophenyl)-1-(4-(t-butyldiphenylsiloxy phenyl)butanol To a solution of aldehyde (1.2 g) (Step III) in THF (10 mL) at 0° was added 2 mL of 0.5M Grignard reagent (prepared from bromide of Step V and Mg in THF). The reaction mixture was warmed to RT and after 1 hr, quenched with pH 7 buffer, extracted with ethyl acetate, and the organic layer was dried and evaporated. Flash chromatography using 10% ethyl acetate/hexane afforded the title compound which was used as such for the next step.

$^1$H NMR: (CD$_3$COCD$_3$) δ: 1.2 (s, 9H), 1.7–1.9 (m, 4H), 2.7 (t, 2H), 4.65 (m, 1H), 6.85 (d, 2H), 7.2–7.85 (m, 16H).

Step VI: Preparation of 4-(4-(4-chlorophenyl)-1-hydroxybutyl)phenol

To a solution of silyl alcohol (Step V) (1.2 g) in THF (10 mL) and acetic acid (0.3 mL) was added tetrabutylammonium fluoride (3 mL of 1M solution). The reaction mixture was stirred 2 hrs, quenched with pH 7 buffer, extracted with ethyl acetate and the organic extract dried and evaporated. Flash chromatography using 25% ethyl acetate/hexane afforded the title compound.

$^1$H NMR: (CD$_3$COCD$_3$) δ: 1.55–1.85 (m, 4H), 2.6–2.75 (t, 3H), 4.0 (d, 1H), 4.55 (m, 1H), 6.75 (d, 2H), 7.15–7.3 (m, 6H), 8.30 (s, 1H).

Step VII: Preparation of methyl ((4-(4-chlorophenyl)-1-(4-hydroxyphenyl)-1-butyl)thio)acetate To a suspension of the alcohol (0.23 g) (Step VI) in CH$_2$Cl$_2$ (5 mL) and methyl thioglycolate (80 μL) was added ZnI$_2$ (10 mg). The mixture was stirred 2 hrs, buffer (pH 7) was added. The mixture was extracted with ethyl acetate, which was dried and evaporated. Flash chromatography using 5% ethyl acetate in toluene afforded the title compound.

$^1$H NMR: (CD$_3$COCD$_3$) δ: 1.5–1.9 (m, 4H), 2.6 (t, 2H), 3.0 (dd, 2H), 3.65 (s, 3H), 4.0 (dd, 1H), 6.8 (d, 2H), 7.1–7.3 (m, 6H), 9.4 (s, 1H).

Step VIII:

Using the procedure of Example 4, Step III and Step IV, the phenol of Step VII, was converted to the title compound. The compound was identical to the compound of Example 12.

Anal. calc'd for C$_{28}$H$_{26}$ClNO$_3$S: C 68.35, H 5.33, Cl 7.21, N 2.85, S 6.52; Found C 67.97, H 5.32, Cl 7.71, N 2.97, S 6.61.

When the 4-chlorobenzaldehyde is replaced by the aldehydes below, the corresponding products are obtained.
2-chlorobenzaldehyde
3-chlorobenzaldehyde
4-methylthiobenzaldehyde
4-bromobenzaldehyde
4-fluorobenzaldehyde 4-methylbenzaldehyde
4-iodobenzaldehyde
4-methoxybenzaldehyde.

EXAMPLE 18

Following the above procedures the following compounds may be prepared:

{[1-(4-(2-quinolinylmethoxy)phenyl)-4-(4-trifluoromethyl)phenyl)butyl]thio}acetic acid;

2-{[1-(4-(2-quinolinylmethoxy)phenyl)-4-(4-(methylthio)phenyl)butyl]thio}propanoic acid;

3-{[4-(4-fluorophenyl)-1-(4-(2-quinolinylmethoxy)phenyl)butyl]thio}propanoic acid;

3-{[4-(4-(methylthio)phenyl)-1-(4-(2-quinolinylmethoxy)phenyl)butyl]thio}propanoic acid;

3-{[4-(4-bromophenyl)-1-(4-(2-quinolinylmethoxy)phenyl)butyl]thio}propanoic acid;

3-{[4-(4-chlorophenyl)-1-(4-(2-quinolinylmethoxy)phenyl)butyl]thio}propanoic acid;

{1-(4-(2-quinolinylmethoxy)phenyl)-4-(4-(trifluoromethyl)phenyl)butyloxy}acetic acid;

{4-(4-fluorophenyl)-1-(4-(2-quinolinylmethoxy)phenyl)butyloxy}acetic acid;

{4-(4-methylthiophenyl)-1-(4-(2-quinolinylmethoxy)phenyl)butyloxy}acetic acid;

{4-(4-bromophenyl)-1-(4-(2-quinolinylmethoxy)phenyl)butyloxy}acetic acid;

3-{1-(4-(2-quinolinylmethoxy)phenyl)-4-(4-trifluoromethyl)phenyl)butyloxy}propanoic acid;

3-{4-(4-fluorophenyl)-1-(4-(2-quinolinylmethoxy)phenyl)butyloxy}propanoic acid;

3-{4-(4-(methylthio)phenyl)-1-(4-(2-quinolinylmethoxy)phenyl)butyloxy}propanoic acid;

3-{4-(4-bromophenyl)-1-(4-(2-quinolinylmethoxy)phenyl)butyloxy}propanoic acid;

3-{4-(4-chlorophenyl)-1-(4-(2-quinolinylmethoxy)phenyl)butyloxy}propanoic acid;

3-{4-(4-chlorophenyl)-1-(4-(2-quinolinylmethoxy)phenyl)butyloxy}acetic acid;

3-{[1-(4-(6-isopropyl-2-quinolinylmethoxy)phenyl)-4-phenylbutyl]thio}propanoic acid;

{[1-(4-(6-methoxy-2-quinolinylmethoxy)phenyl)-4-phenylbutyl]thio}acetic acid;

3-{[1-(4-(6-methoxy-2-quinolinylmethoxy)phenyl)-4-phenylbutyl]thio}propanoic acid;

{[1-(4-(6-fluoro-2-quinolinylmethoxy)phenyl)-4-phenylbutyl]thio}acetic acid.

EXAMPLE 19

Using the methodology of method D, the following compounds are prepared:

5-[4-(2-quinolinylmethoxy)phenyl]-7-phenylheptanoic acid;

5-[4-(2-quinolinylmethoxy)phenyl]-8-phenyloctanoic acid;

2-methyl-5-[4-(2-quinolinylmethoxy)phenyl]-8-phenyloctanoic acid.

EXAMPLE 21

[[2-Phenylmethoxy-1-(4-(2-quinolinylmethoxy)phenyl)ethyl] thio]acetic acid

Step 1: Preparation of 1-hydroxy-1-(4-(2-quinolinylmethoxy)phenyl)ethanol

A mixture containing 2-(chloromethyl)quinoline hydrochloride (2.68 g), 2-hydroxy-2-(4-hydroxyphenyl)ethanol (1.74 g) and anhydrous $K_2CO_3$ (4.70 g) was stirred at room temperature in dry N,N-dimethylformamide (DMF) for 3 days. DMF was removed under reduced pressure and the residue was partitioned between $CH_2Cl_2$ and water. The aqueous phase was re-extracted with $CH_2Cl_2$ and the combined organic phase was washed with brine, dried and concentrated. The title compound was obtained after recrystallization from methanol/ethyl acetate/hexane.

Step 2: Preparation of [[1,2-diphenylmethoxy-1-(4-(2-quinolinylmethoxy)phenyl]ethane At 0° C., 50% NaH in oil (37 mg) was added portionwise to a solution of 1-hydroxy-1-(4-2(-quinolinylmethoxy)phenyl)ethanol (Step 1) (104 mg) and benzyl bromide (92 mg). Stirring was continued for 18 h and the reaction was quenched with 25% aqueous NH₄OAc. The product was extracted with EtOAc, dried over MgSO₄ and purified by flash chromatography on silica gel using EtOAc:hexane (1:4) to give the title compound as an oil.

Step 3:

To a mixture of the ether (151 mg) (Step 2) and thioglycolic acid (31 μL) in $CH_2Cl_2$ at 0° C. was added $BF_3/OEt_2$ (117 μL) dropwise. The mixture was stirred at 0° C. for 1 h and poured onto 25% aqueous NH₄OAc, extracted with $CH_2Cl_2$ and the organic phase was dried and evaporated. Chromatography on silica gel using ethyl acetate/hexane containing 0.1% AcOH afforded the title compound.

$^1$H NMR (CDCl$_3$) δ: 3.01 (d, 1H, J=15), 3.18 (d, 1H, J=15), 3.78 (d, 2H, J=7), 4.29 (t, 1H, j=7), 4.52 (dd, 2H, J=14), 5.37 (s, 2H), 6.98 (d, 2H, J=9), 7.20–7.38 (m, 7H), 7.50–7.90 (m, 4H), 8.09 (d, 1H, J=8), 8.20 (d, 1H, J=8).

EXAMPLE 22

[[2-(4-Chlorophenylmethoxy)-1-(4-(2-quinolinylmethoxy)phenyl)ethyl]thio]acetic acid Using the procedure of Example 21 but replacing benzyl bromide with 4-chlorobenzyl chloride in Step 2, there was obtained the title compound.

$^1$H NMR (CDCl$_3$) δ: 3.07 (d, 1H, J=15), 3.24 (d, 1H, J=15), 3.79 (d, 2H, J=7), 4.36 (t, 1H, J=7), 4.48 (s, 2H), 5.40 (s, 2H), 7.12–7.40 (m, 6H), 7.56 (t, 1H, J=5), 7.66–7.90 (m, 3H), 8.15 (d, 1H, J=6), 8.24 (d, 1H, J=6).

EXAMPLE 23

[[2-(4-Trifluoromethylphenylmethoxy)-1-(4-(2-quinolinylmethoxy)phenyl)ethyl]thio]acetic acid Using the procedure of Example 21 but replacing benzylchlrodie with 4-trifluoromethylbenzyl chloride in Step 2, there was obtained the title compound.

$^1$H NMR (CDCl$_3$): 3.06 (d, 1H, J=15), 3.23 (d, 1H, J=15), 3.81 (d, 2H, J=7), 4.39 (t, 1H, J=7), 4.56 (s, 2H), 5.41 (s, 2H), 6.99 (d, 2H, J=8.5), 7.28 (d, 2H, J=8.5), 7.37 (d, 2H, J=8), 7.85–7.52 (m, 6H), 8.08 (d, 1H, J=8.5), 8.20 (d, 1H, J=8.4).

EXAMPLE 24

(4-(4-Chlorophenyl)-1-(4-)2-quinolinylmethoxy)phenyl)butoxy)acetic acid

Step 1: Preparation of 4-((2-methyl-2-propyl)diphenylsilyloxy)benzaldehyde

At 0° C., tert-butyldiphenylchlorosilane (50 g) was added slowly to a solution of p-hydroxybenzaldehyde (22 g) and Et$_3$N (42 mL) in 1,2-dichloroethane (400 mL) and the mixture was stirred at room temperature a few hours. After the usual work up, the product was purified by flash chromatography on silica using EtOAc:-hexane 1:10 and was used as such for Step 2.

Step 2: Preparation of 1-(4-((2-methyl-2-propyl)diphenylsilyloxy)phenyl)-4-(4-chlorophenyl)-1-butanol Using the procedure of Example 1, Step 2, the Grignard reagent prepared from 1-(3-bromopropyl)-4-chlorobenzene was added to the benzaldehyde of Step 1. The title compound so obtained was used as such in the next step.

Step 3: Preparation of 4-(4-chlorophenyl)-1-(4-hydroxyphenyl)-1-butanol

At 0° C., 1M tetrabutylammonium fluoride (100 mL) was added to a solution of the silyl ether of Step 2 (34 g) and AcOH (15 mL) in THF (200 mL) and the reaction mixture was stirred at 0° C. 2.5 hours. 25% aqueous NH4OAc was then added and the product was extracted with EtOAc, dried over MgSO4 and purified by a swish in EtOAc:hexane 1:2. The title compound so obtained was used as such for the next step.

Step 4: Preparation of methyl (4-(4-chlorophenyl)-1-(4-hydroxyphenyl)-1-butoxy)acetate A mixture of the alcohol of Step 3 (138 mg), methyl hydroxyacetate (80 μL), dry fused ZnCl2 (82 mg) in 1,2-dichloroethane (5 mL) was heated to 80° C. for an hour. The title compound was extracted with EtOAc, dried over Na2SO4 and purified by flash chromatography on silica using EtOAc:toluene 5:95 and 7.5:92.5. (For reference, see J. Org. Chem., 52 3917 (1987)).

$^1$H NMR (CDCl3): 1.47–2.00 (m, 4H), 2.56 (t, 2H), 3.72 (s, 3H), 3.83 (d, 1H), 3.96 (d, 1H), 4.30 (t, 1H), 5.19 (br s, 1H, OH), 6.82 (d, 2H), 7.06 (d, 2H), 7.14 (d, 2H), 7.21 (d, 2H) ppm.

Step 5: Preparation of methyl (4-(4-chlorophenyl)-1-(4-(2-quinolinylmethoxy)phenyl)butoxy acetate The phenol of Step 4 (74 mg, 212 μmoles), 2-(chloromethyl)quinoline hydrochloride (75 mg, 1.5 equiv.), and K2CO3 (121 mg, 4 equiv.) were stirred together in DMF (2 mL) for 4 days. 25% Aqueous NH4OAc was then added and the product was extracted with EtOAc, dried over Na2SO4 and purified by flash chromatography on silica using EtOAc:toluene 5:95 and 7.5:92.5. It was used as such for the next step.

Step 6

The ester of Step 5 was hydrolyzed by NaOH as in Example 1, Step 4 and the final product was purified by flash chromatography on silica using acetone:-toluene:AcOH 7.5:92.5:1.

Anal. calc'd for $C_{28}H_{26}ClNO_4$: C, 70.66; H, 5.51; N, 2.94; Found: C, 70.69; H, 5.41; N, 2.85.

EXAMPLE 25

1.5-Di-(4-chlorophenyl)-2-(4-(2-quinolinylmethoxy)-phenyl)pent-2-ylthioacetic acid Step 1: Preparation of 4-(4-chlorophenyl)-1-(4-(2-quinolinylmethoxy)phenyl)-1-butanone Following the procedure of Example 1, Step II but replacing 1-bromo-3-phenylpropane with 3-(4-chloro)-phenylpropyl bromide) (11.65 g) in CHCl3 at room temperature and adding MnO2 (11.65 g), the analogous alcohol was prepared.

After 21 hours, a second portion of MnO2 (5 g) was added, followed 6 hours later by a third 5 g portion. The reaction mixture was filtered through a bed of celite after a total of 43 hours of stirring, and the filter cake was washed several times with CHCl3. The filtrate was evaporated and the product was recrystallized from ethyl acetate to give the title compound as a white solid, m.p. 140°–142° C.

Step 2: Preparation of 1,5-di(4-chlorophenyl)-2-(4(2-quinolinylmethoxy)phenyl)-2-pentanol To a solution of ketone from Step 1 (1.09 g, 2.62 mmol) in dry THF (15 mL) was added a solution of 4-chlorobenzyl magnesium chloride (1.86M, 1.55 mL, 2.88 mmol). The reaction was quenched after 5 hours by the addition of saturated NH4Cl solution (5 ml), followed by brine (20 ml). The product was extracted with EtOAc and the organic layer was washed with H2O and brine. The solvent was removed under vacuum, and the residue was purified by flash chromatography (gradient of 1:20, 1:5, 1:2 EtOAc/hexane). A pale yellow syrup, which gradually crystallized, was obtained.

This material was used as such, although a small amount was stirred with 1:5 EtOAc/hexane to give the title compound as a white solid, m.p. =123°–124° C.

Step 3:

To a solution of tertiary alcohol from Step 2 (0.32 g, 0.59 mmol) and mercaptoacetic acid (45 μL, 0.65 mmol) in CH2Cl2 (5 ml) at 0° C. was added BF3/OEt2 (0.22 mL, 1.7 mmol). The pale orange solution was stirred for three hours at 0° C. Saturated NH4Cl solution (5 ml) and H2O (2 ml) was then added, and the product was extracted twice with CH2Cl2. The organic layer was washed with H2O, dried (Na2SO4), and evaporated to give a syrup. Purification was effected by flash chromatography (1:5 EtOAc/hexane with 1% HOAc). The resulting product was triturated with a small amount of CH2Cl2 to give a white solid, m.p. 173°–176° C. (dec).

EXAMPLE 26

1,5-Di-(4-chlorophenyl)-2-(4-(2-quinolinylmethoxy)-phenyl)pent-2-yl-(3-thiopropanoic acid Using the procedure of Example 25 but replacing mercaptoacetic acid with 3-mercaptopropanoic acid in Step 3, there was obtained the title compound, m.p. 180°–183° C. (dec.)

EXAMPLE 27

1.5-Di-(4-chlorophenyl)-2-(4-(2-quinolinylmethoxy)-phenyl)pent-2-yl-(2,2-dimethyl-3-thiopropanoic acid Using the procedure of Example 25 but replacing mercaptoacetic acid with 2,2-dimethyl-3-mercaptopropanoic acid in Step 3, there was obtained the title compound, m.p. 174°–176° C.

EXAMPLE 28

1.5-Di-(4-chlorophenyl)-2-(4-(2-quinolinylmethoxy)-phenyl)pent-2-yl-(2-thiopropanoic acid)

Using the procedure of Example 25 but replacing mercaptoacetic acid with 2-mercaptopropanoic acid in Step 3, there was obtained the title compound.

$^1$H NMR: δ 8.24 (d, 1H, J=8.5 Hz), 8.14 (d, 1H, J=8.3 Hz), 7.85 (d, 1H, J=8.1 Hz), 7.82–7.79 (m, 2H), 7.61–7.55 (m, 1H), 7.37 (d, 2H, J=8.8 Hz), 7.17 (d, 2H, J=8.40 Hz), 5.39 (s, 2H), 3.16 (d, 1H, J=13.5 Hz), 2.97 (d, 1H, J=13.6 Hz), 2.88–2.77 (m, 1H), 2.54–2.40 (m, 2H), 2.20–1.65 (complex m, 4H), 1.21 (d, 3H, J=7.3 Hz).

EXAMPLE 29

1,5-Di-(4-chlorophenyl)-2-(4-(2-quinolinylmethoxy)-phenyl)pent-2-yl-(3-thiobutanoic acid Step 1: Preparation of ethyl-1,5-di-(4-chlorophenyl-2-(4-(2-quinolinylmethoxy)phenyl)pent-2-yl-(3-mercaptobutanoate)

Using the procedure of Example 25 but replacing mercaptoacetic acid with ethyl mercaptobutanoate in Step 3, there was obtained the title compound.

1H NMR: δ 8.23 (d, 1H, J=8.8 Hz), 8.10 (d, 1H, J=8.8 Hz), 7.88–7.83 (m, 1H), 7.81–7.68 (m, 2H), 7.61–7.53 (m, 1H), 7.35–7.20 (m, 4H), 7.12–6.90 (m, 6H), 6.58 (d, 2H, J=8.5 Hz), 5.38 (s, 2H), 4.08 (q, 2H, J=5.0 Hz), 3.10 (d, 1H, J=13.0 Hz), 2.99 (d, 1H, J=13.0 Hz), 2.64–2.52 (m, 2H), 2.33–2.24 (m, 2H), 2.20–2.05 (m, 2H), 1.99–1.88 (m, 1H), 1.81–1.62 (m, 5H), 1.22 (t, 3H, J=6.5 Hz).

Step 2:

To a solution of ester from Step 1 (0.44 g, 0.65 mmol) in a mixture of MeOH (2 mL), THF (2 mL), and H$_2$O (0.5 mL) was added 10M NaOH solution (0.13 mL, 1.3 mmol). After stirring for 5½ hours, the solution was acidified with HOAc and was then concentrated under vacuum. The remaining aqueous residue was extracted with CH$_2$Cl$_2$, and the organic phase was washed with H$_2$O and evaporated to dryness. Following purification by flash chromatography (1:5 EtOAc/hexane), the resulting pale yellow syrup was triturated with 1:5 EtOAc/hexane to give a white solid, m.p.=121°–123° C.

EXAMPLE 30

7-(Chlorophenyl)-4-(4-(2-quinolinylmethoxy)phenyl)-hept-2-en-4-ylthioacetic acid Step 1: Preparation of 7-(4-chlorophenyl)-4-(4-(2-quinolinylmethoxy)phenyl)hept-1-ene-4-ol To a solution of ketone from Example 25, Step 1 (1.5 g, 3.61 mmol) in dry THF (15 mL) at 0° C. was added a 1M solution of allyl magnesium bromide (4.3 mL, 4.3 mmol). The reaction mixture was stirred for 45 minutes at 0° C., at which point saturated NH$_4$Cl solution (15 mL) was added, and the product was extracted with EtOAc. The organic layer was washed with water and brine, and was then evaporated to dryness. Purification by flash chromatography (gradient of 1:20, 1:10, 1:5 EtOAc/hexane) gave a pale yellow syrup which was triturated with 1:4 ether/hexane to give the title compound as a white solid, m.p.=87°–88° C.

Step 2:

Using the procedure of Example 25, Step 3 the title compound was obtained as a foam.

1H NMR: δ 8.24 (d, 1H, J=8.8 Hz), 8.13 (d, 1H, J=8.8 Hz), 7.85 (d, 1H, J=8.5 Hz), 7.80–7.68 (m, 2H), 7.62–7.53 (m, 1H), 7.42–7.35 (m, 2H), 7.23–7.17 (m, 2H), 7.08–6.92 (m, 4H), 5.84–5.66 (m, 1H), 5.37 (s, 2H), 5.13–5.02 (m, 2H), 2.89 (s, 2H), 2.77–2.68 (m, 2H), 2.58–2.46 (m, 2H), 1.97 (m, 1H), 1.83–1.62 (m, 1H), 1.50–1.31 (m, 1H).

EXAMPLE 31

1-(4-Chlorophenyl)-4-(4-(2-quinolinylmethoxy)phenyl)-pent-4-ylthioacetic acid

Step 1; Preparation of 5-(4-chlorophenyl)-2-(4-(2-quinolinylmethoxy)phenyl)pentan-2-ol Using the procedure of Example 25, Step 2, but replacing 4-chlorobenzyl magnesium chloride with methyl cerium dichloride there was obtained the title compound as a white solid, m.p.=110°–112° C.

Step 2:

Using the procedure of Example 25, Step 3, the title compound was obtained as a white foam.

1H NMR: δ 8.22 (d, 1H, J=8.5 Hz), 8.13 (d, 1H, J=8.4 Hz), 7.87–7.67 (m, 3H), 7.62–7.54 (m, 1H), 7.35 (d, 2H, J=8.9 Hz), 7.20–7.15 (m, 2H), 7.02–6.90 (m, 4H), 6.00–5.00 (bs, 1H), 5.35 (s, 2H), 2.99 (s, 2H), 2.60–2.40 (m, 2H), 2.11–1.95 (m, 1H), 1.95–1.80 (m, 1H), 1.80–1.56 (m, 1H), 1.69 (s, 3H), 1.49–1.28 (m, 1H).

EXAMPLE 32

1,7-Diphenyl-4-(4-(2-quinolinylmethoxy)phenyl)hept-4-yl-thioacetic acid

Using the procedure of Example 25 but in Step 1 replacing 2-((4-(1-hydroxy-4-(4-chlorophenyl)butyl)-phenoxy)-methyl)quinoline with 2-((4-(1-hydroxy-4-phenyl-butyl)phenoxy)methyl)quinoline from Example 1 and replacing 4-chlorobenzyl magnesium chloride with 3-phenylpropyl magnesium bromide in Step 2, there was obtained the title compound.

1H NMR: δ 1.18–1.49 (m, 2H), 1.50–1.76 (m, 2H), 1.76–2.04 (m, 4H), 2.54 (t, 4H, J=6), 2.76 (s, 2H), 5.32 (s, 2H), 6.87 (d, 2H, J=8), 7.00–7.40 (m, 12H), 7.50–7.90 (m, 4H), 8.15 (d, 1H, J=8), 8.21 (d, 1H, J=8).

EXAMPLE 33

1,5-Diphenyl-2-(4-(2-quinolinylmethoxy)phenyl)pent-2-ylthioacetic acid

Using the procedure of Example 32 but replacing 3-phenylpropylmagnesium bromide with benzylmagnesium chloride, there was obtained the title compound.

1H NMR: δ 1.60–2.1 (M, 4H), 2.30 (S, 2H), 2.54 (M, 2H), 3.04 (d, 1H, J=12), 3.10 (d, 1H, J=12), 5.36 (s, 2H), 6.60–8.30 (M, 20H).

EXAMPLE 34

1,6-Diphenyl-3-(4-(2-quinolinylmethoxy)phenyl)hex-3-ylthioacetic acid

Using the procedure of Example 25 but replacing 2-((4-(1-hydroxy-4-(4-chloro)phenylbutyl)phenoxy)methyl)quinoline with 2-((4-(1-hydroxy-3-phenylpropyl)-phenoxy)methyl)quinoline in Step 1 and replacing 4-chlorobenzyl magnesium bromide with 2-phenylethylmagnesium bromide in Step 2, there was obtained the title compound.

1H NMR: δ 2.20–2.65 (m, 6H), 2.70–2.92 (m, 2H), 2.96 (s, 2H), 5.24 (s, 2H), 6.99 (s, 2H, J=7), 7.05–7.20 (m, 10H), 7.46–7.66 (m, 3H), 7.66–7.94 (m, 3H), 7.13 (d, 1H, J=8), 7.22 (d, 1H, J=8).

EXAMPLE 35

((1-(((4-Chlorophenyl)methyl)thio)-1-(4-(2-quinolinylmethoxy)phenyl)methyl)thio)acetic acid, sodium salt Step 1: Preparation of methyl ((1-(((4-chlorophenyl)-methyl)thio)-1-(4-(2-quinolinylmethoxy)phenyl)methyl)thio)acetate At 0° C., BF$_3$/Et$_2$O (380 μL, 2.3 equiv.) was added to a solution of 4-(2-quinolinylmethoxy)benzaldehyde (Example 1, Step 1, 352 mg, 1.34 mmoles), methyl thioglycolate (130 μL, 1.1 equiv.) and 4-chlorobenzyl mercaptan (195 μL, 1.1 equiv.) in CH$_2$Cl$_2$ (7 mL) and the mixture was stirred at 0° C. an hour and at room temperature 15 minutes. 25% Aqueous NH$_4$OAc was then added at 0° C. and the products were extracted with EtOAc, dried over Na$_2$SO$_4$ and separated by flash chromatography on silica using EtOAc:toluene 2.5:97.5 and 5:95 to yield the title compound.

$^1$H NMR (CDCl$_3$) δ: 3.06 (d, 1H), 3.28 (d, 1H), 3.63 (s, 3H), 3.65 (d, 1H), 3.86 (d, 1H), 4.81 (s, 1H), 5.37 (s, 1H), 6.97 (d, 2H), 7.14–7.32 (m, 6H), 7.55 (dd, 1H), 7.66 (d, 1H), 7.75 (dd, 1H), 7.84 (d, 1H), 8.08 (d, 1H), 8.20 (d, 1H).

Step 2:

The ester of Step 1 was hydrolyzed as in Example 1, Step 4 and the resulting acid was purified by flash chromatography on silica using EtOAc:toluene:AcOH 15:85:1 and 20:80:1. It was then converted to the sodium salt by addition of 1.0 equiv. of 1.0N NaOH to an EtOH solution of the acid. The ethanol was evaporated, the salt was dissolved in water and freeze-dried to yield the title compound.

Anal. calc'd for C$_{26}$H$_{21}$ClNO$_3$S$_2$Na/H$_2$O: C, 58.25; H, 4.32; N, 2.61; Na, 4.29; Found: C, 58.42; H, 4.47; N, 2.84; Na, 3.82.

EXAMPLE 36

((1-(4-Pyridinylthio)-1-(4-(2-quinolinylmethoxy)-phenyl)methyl)thio)acetic acid

Using the procedure of Example 35, but substituting 4-mercaptopyridine for 4-chlorobenzyl mercaptan in Step 1, the title acid was prepared.

$^1$H NMR (CD$_3$COCD$_3$/CD$_3$SOCD$_3$) δ: 3.25 (d, 1H), 3.44 (d, 1H), 5.48 (s, 2H), 5.95 (s, 1H), 7.12 (d, 2H), 7.37 (d, 2H), 7.55 (d, 2H), 7.61 (dd, 1H), 7.71 (d, 1H), 7.78 (dd, 1H), 7.97 (d, 1H), 8.03 (d, 1H), 8.35–8.42 (m, 3H).

EXAMPLE 37

((1-(Phenylmethyl)thio-1-(4-(2-quinolinylmethoxy)-phenyl)methyl)thio)acetic acid, sodium salt Using the procedure of Example 35 and replacing 4-chlorobenzylmercaptan with benzylmercaptan, there was obtained the title compound.

$^1$H NMR (CD$_3$SOCD$_3$/CD$_3$COCD$_3$) δ: 3.25 (dd, 2H), 3.8 (dd, 2H), 5.20 (s, 1H), 5.35 (3, 2H), 7.0–8.4 (m, 15H).

EXAMPLE 38

((1-(2-Phenylethyl)thio-1-(4-(2-quinolinylmethoxy)-phenyl)methyl)thio)acetic acid Using the procedure of Example 35 and replacing methyl thioglycolate with thioglycolic acid and 4-chlorobenzyl mercaptan with 2-phenethylmercaptan, there was obtained the title acid.

Anal. calc'd for C$_{27}$H$_{25}$NO$_3$S$_2$: C, 68.18, H, 5.30; N, 2.94; S, 13.48; Found: C, 68.11; H, 5.36; N, 2.97; S, 13.43.

What is claimed is:

1. A compound of formula:

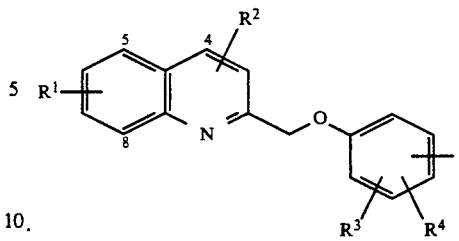

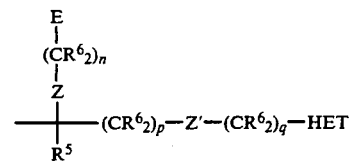

wherein:
Z is CH$_2$, O, or S;
Z' is O or S;
m is 2–4;
n is 1–5;
p is 0–4;
q is 0–4;
E is CO$_2$R$^8$, CO$_2$R$^{12}$, —CONHSO$_2$R$^9$, —CONR$^{10}$R$^{10}$, or —NHSO$_2$R$^9$;
HET is 2-, 3-, or 4-pyridyl or 2- or 3-thienyl, each of which has two R$^{16}$ substituents;
R$^1$ and R$^2$ are independently halogen, C$_1$–C$_6$ alkyl, C$_2$–C$_6$ alkenyl, C$_2$–C$_6$ alkynyl, —CF$_3$, —OR$^{10}$, —SR$^9$, —S(O)$_2$R$^9$, —NR$^{10}$R$^{10}$, —CHO, —CO$_2$R$^8$, —(C=O)R$^{11}$, —C(OH)R$^6$R$^6$, —CN, NO$_2$, N$_3$, substituted or unsubstituted phenyl, or substituted or unsubstituted C$_1$–C$_6$ phenylalkyl;
R$^3$ and R$^4$ are independently H, halogen, C$_1$–C$_6$ alkyl, C$_2$–C$_6$ alkenyl, C$_2$–C$_6$ alkynyl, —CF$_3$, —OR$^{10}$, —SR$^9$, —S(O)$_2$R$^9$, —NR$^{10}$R$^{10}$, —CHO, —CO$_2$R$^8$, —(C=O)R$^{11}$, —C(OH)R$^6$R$^6$, —CN, NO$_2$, N$_3$, substituted or unsubstituted phenyl, or substituted or unsubstituted C$_1$–C$_6$ phenylalkyl;
R$^5$ is H, lower alkyl, or phenyl lower alkyl;
each R$^6$ is independently H or lower alkyl, or two R$^6$'s may be joined to form a ring of 3–6 atoms;
R$^8$ is H, C$_1$–C$_6$ alkyl, substituted or unsubstituted phenyl, or substituted or unsubstituted benzyl;
R$^9$ is CF$_3$, C$_1$–C$_6$ alkyl, substituted or unsubstituted phenyl, or C$_1$–C$_6$ phenylalkyl;
R$^{10}$ is R$^9$, H, or —(C=O)R$^{11}$, or two R$^{10}$ groups joined to the same nitrogen may form a ring selected from the group consisting of pyrrolidine, piperidine, morpholine, thiamorpholine, piperazine, and N-methylpiperazine;
R$^{11}$ is H, C$_1$–C$_6$ alkyl, C$_2$–C$_6$ alkenyl, C$_2$–C$_6$ alkynyl, CF$_3$, unsubstituted phenyl, or unsubstituted C$_1$–C$_6$ phenylalkyl;
R$^{12}$ is —CH$_2$CONR$^{10}$R$^{10}$;
R$^{15}$ is C$_1$ to C$_3$ alkyl, halogen, CF$_3$, N$_3$, C$_1$ to C$_3$ alkoxy, C$_1$ to C$_3$ alkylthio, or C$_1$ to C$_3$ alkylcarbonyl;
R$^{16}$ is H or R$^{15}$;
R$^{18}$ is R$^5$, lower alkenyl, lower alkynyl, substituted phenyl-lower alkyl, halo-lower alkyl, halo-lower alkenyl, or halo-lower alkynyl;
substituted means the benzene ring carries 1 or 2 R$^{15}$ substituents; and the pharmaceutically acceptable salts thereof.

2. A pharmaceutical composition comprising a therapeutically effective amount of a compound of claim 1 and a pharmaceutically acceptable carrier.